United States Patent
Bose et al.

(10) Patent No.: US 12,084,493 B2
(45) Date of Patent: Sep. 10, 2024

(54) METHODS OF TREATING INFLAMMATION ASSOCIATED AIRWAY DISEASES AND VIRAL INFECTIONS

(71) Applicant: Washington State University, Pullman, WA (US)

(72) Inventors: Santanu Bose, Pullman, WA (US); Philippe Tessier, Quebec (CA)

(73) Assignee: Washington State University, Pullman, WA (US)

( * ) Notice: Subject to any disclaimer, the term of this patent is extended or adjusted under 35 U.S.C. 154(b) by 51 days.

(21) Appl. No.: 16/994,882

(22) Filed: Aug. 17, 2020

(65) Prior Publication Data

US 2021/0032323 A1 Feb. 4, 2021

Related U.S. Application Data

(63) Continuation-in-part of application No. 15/986,382, filed on May 22, 2018, now Pat. No. 10,745,474, which is a continuation of application No. 14/985,591, filed on Dec. 31, 2015, now Pat. No. 10,005,833.

(60) Provisional application No. 63/003,784, filed on Apr. 1, 2020, provisional application No. 62/099,376, filed on Jan. 2, 2015.

(51) Int. Cl.
*A61K 39/395* (2006.01)
*C07K 16/24* (2006.01)
*A61K 39/00* (2006.01)

(52) U.S. Cl.
CPC ........ *C07K 16/24* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 10,005,833 B2 | 6/2018 | Bose | |
| 10,745,474 B2 | 8/2020 | Bose | |
| 2004/0259934 A1* | 12/2004 | Olsen | A61K 31/381 514/447 |
| 2014/0336159 A1* | 11/2014 | Clarke | A61K 45/06 514/557 |
| 2015/0210768 A1* | 7/2015 | Roth | A61P 37/08 424/139.1 |
| 2016/0083456 A1 | 3/2016 | Wittekind | |

FOREIGN PATENT DOCUMENTS

WO WO2012155049 11/2012

OTHER PUBLICATIONS

Zhang et al., "Progress and Prospects on Vaccine Development against SARS-CoV-2," Vaccines 8: 153 (Year: 2020).*

(Continued)

*Primary Examiner* — M Franco G Salvoza
(74) *Attorney, Agent, or Firm* — Barnes & Thornburg LLP

(57) ABSTRACT

The present disclosure provides methods of treating a pathogen-induced lung inflammation in a subject are provided in which an anti-S100A9 antibody is administered to a subject. Methods of treating a respiratory virus infection by administering an anti-S100A9 antibody are also provided.

19 Claims, 23 Drawing Sheets

Specification includes a Sequence Listing.

(56) References Cited

OTHER PUBLICATIONS

Li et al., "Updated Approaches against SARS-CoV-2," Antimicrobial Agents and Chemotherapy, vol. 64, Issue 6:e00483-20 (Year: 2020).*
Okabayashi et al., "Cytokine Regulation in SARS Coronavirus Infection Compared to Other Respiratory Virus Infections," Journal of Medical Virology, 78:417-424 (Year: 2006).*
Sharma et al., Emerging Microbes and Infections, 2, e54 (2013).
Goldstein, Virulence, 1(4):295-298 (2010).
Kunisaki et al., Lancet Infect Dis, (8):493-504 (2010).
Chen et al., PLOS One, 9(3):e92500 (2014).
Ali Alejo, et al, "Chemokines cooperate with TNF to provide protective anti-viral immunity and to enhance inflammation", Nature Communications, vol. 9(1):1790, 2018, pp. 1-16.
Santanu Bose, et al, "Temporal activation of NF-kB regulates an interferon-independent innate antiviral response against cytoplasmic RNA viruses", Proceedings of the National Academy of Sciences (PNAS), vol. 100(19), 2003, pp. 10890-10895.
Jesse Fajnzylber, et al, "SARS-CoV-2 viral load is associated with increased disease severity and mortality", Nature Communications, vol. 11(1):5493, 2002, pp. 1-9.
Jodi F. Hedges, et al, "An ADAM17-Neutralizing Antibody Reduces Inflammation and Mortality While Increasing Viral Burden in a COVID-19 Mouse Model", Frontiers in Immunology, vol. 13:918881, 2022, pp. 1-9.
Barbara J. Mann, et al, "Improved survival of SARS COV-2-infected K18-hACE2 mice treated with adenosine A2AR agonist", Heliyon, vol. 9(8):e19226, 2023, pp. 1-9.
Mar Masiá, et al., "Impact of interleukin-6 blockade with tocilizumab on SARS-CoV-2 viral kinetics and antibody responses in patients with COVID-19: A prospective cohort study", EBioMedicine, vol. 60:102999, 2020, pp. 1-9.
Jennifer Oyler-Yaniv, et al., "TNF controls a speed-accuracy tradeoff in the cell death decision to restrict viral spread", Nature Communications, vol. 12(1):2992, 2021, pp. 1-11.
Janet Ruby, et al., "Antiviral Activity of Tumor Necrosis Factor (TNF) Is Mediated via p55 and p75 TNF Receptors", Journal of Experimental Medicine (JEM), vol. 186(9), 1997, pp. 1591-1596.
Srikanth Sadhu, et al., "IL-9 aggravates SARS-CoV-2 infection and exacerbates associated airway inflammation", Nature Communications, vol. 14(1):4060, 2023, pp. 1-16.
Sang Heui Seo, et al, "Tumor Necrosis Factor Alpha Exerts Powerful Anti-Influenza Virus Effects in Lung Epithelial Cells", Journal of Virology, vol. 76(3), 2002, pp. 1071-1076.
Qi Zuo, et al, "Role of IL-6-IL-27 Complex in Host Antiviral Immune Response", The Journal of Immunology, vol. 20(2), 2021, pp. 577-589.

* cited by examiner

METHODS OF TREATING INFLAMMATION ASSOCIATED AIRWAY DISEASES AND VIRAL INFECTIONS

This application is a continuation-in-part of U.S. patent application Ser. No. 15/986,382, filed on May 22, 2018, which is a continuation of U.S. patent application Ser. No. 14/985,591, filed Dec. 31, 2015, which claims the benefit under 35 U.S.C. § 119(e) of U.S. Provisional Application Ser. No. 62/099,376, filed on Jan. 2, 2015, and the entire disclosures of all are incorporated herein by reference. This application also claims the benefit under 35 USC § 119(e) of U.S. Provisional Application Ser. No. 63/003,784, filed on Apr. 1, 2020, the entire disclosure of which is incorporated herein by reference.

GOVERNMENT RIGHTS

This invention was made with government support under Grant No. 5R01AI083387, awarded by NIH. The government has certain rights in the invention.

REFERENCE TO SEQUENCE LISTING SUBMITTED ELECTRONICALLY

The official copy of the sequence listing is submitted electronically via EFS Web as an ASCII formatted sequence listing with a file named "321996_ST25.txt", created on, Aug. 17, 2020, and having a size of 4.28 kilobytes, and is filed concurrently with the specification. The sequence listing contained in this ASCII formatted document is part of the specification and is herein incorporated by reference in its entirety.

BACKGROUND

Influenza, commonly known as "the flu," is an infectious disease caused by the influenza virus. The most common symptoms include: a high fever, runny nose, sore throat, muscle pains, headache, coughing, and feeling tired. These symptoms typically begin two days after exposure to the virus and most last less than a week. However, the cough may last for more than two weeks. Complications of influenza may include viral pneumonia, secondary bacterial pneumonia, sinus infections, and worsening of previous health problems such as asthma or heart failure. The lung disease severity following influenza A virus (IAV) infection is dependent on the extent of inflammation in the respiratory tract. Severe inflammation in the lung manifests in development of pneumonia. Therefore, it is critical to identify cellular factors and dissect the molecular/cellular mechanism controlling inflammation in the respiratory tract during IAV infection. There remains a need for compositions and methods to reduce inflammation during influenza A infection.

Furthermore, the recent outbreak of coronavirus infected disease (COVID-19) has claimed a great number of lives and affected even more individuals worldwide. The World Health Organization (WHO) has declared the disease as a pandemic and many countries all over the world have struggled to control the spread of the infection and as well as the treatment of the exponentially growing numbers of patients. Coronavirus infected patients, such as coronavirus SARS-CoV-2 infected patients, are susceptible to disease states such as pneumonia which manifests due to exaggerated airway inflammation. Pneumonia causes severe lung tissue damage, fluid accumulation (edema), and death. With respect to COVID-19 patients, the virus typically causes flu-like symptoms including a fever and cough, wherein it usually starts with a fever, followed by a dry cough. After a week or so, the infection can lead to shortness of breath, with a high percentage of patients requiring hospital treatment.

A recent study of lung bronchoalveolar immune cells in critically ill COVID-19 patients revealed high expression of S100A9 in inflammatory monocytes collected from the respiratory tract of the patients (Liao et al., Nature Medicine, 2020; 26:842-844, incorporated by reference herein in its entirety). As S100A9 is one of the most upregulated genes in Coronavirus infections, S100A9 represents a clinical target in patients infected with Coronavirus, including COVID-19.

RNA viruses such as COVID-19 are prone to frequent mutations and therefore vaccines and anti-viral therapeutics may not be effective against evolved strains of COVID-19 or other coronaviruses that may emerge in human populations in the near future. Therefore, it is critical to identify cellular factors and dissect the molecular/cellular mechanism controlling inflammation in the respiratory tract during this viral infection.

Accordingly a need exists for compositions and methods to reduce inflammation caused by human coronavirus infected diseases, including COVID-19 and highly virulent mutant viral strains arising from COVID-19. The embodiments described herein are directed to such a need.

SUMMARY

Certain embodiments are directed to methods for treating pathogen-induced lung inflammation in a subject comprising administering an antibody that neutralizes S100A9 activity (anti-S100A9 antibody) to the subject. Administration of an antibody that neutralizes S100A9 reduces or ameliorates lung inflammation and infection associated lung disease. In certain aspects the pathogen is a respiratory virus, bacteria, or fungus. Respiratory viruses include, but are not limited to Respiratory Syncytial Virus (RSV), Influenza virus (types A, B, C), Parainfluenza viruses (human prainfluenza viruses type I, II and III), Adenoviruses, Rhinoviruses, Human metapneumoviruses, and Coronaviruses (e.g. SARS).

Respiratory viruses include, but are not limited to, COVID-19, Severe Acute Respiratory Syndrome (SARS CoV-2), Middle East Respiratory Syndrome Coronavirus (MERS-Coy), and mutant viral strains arising from COVID-19.

Respiratory bacteria and fungus include, but are not limited to *Streptococcus pyogenes* (Group A), *Haemophilus influenza, Bordetella pertussis, Moraxella catarrhalis, Streptococcus pneumoniae* (pneumococcus), *Staphylococcus aureus, Legionella pneumophila, Klebsiella pneumonia, Pseudomonas aeruginosa, Burkholderia cepacia, Mycoplasma pneumonia, Mycobacterium tuberculosis, Chlamydia Pneumoniae, Candida albicans, Coccidioides immitis, Histoplama capsulatum, Blastomyces dermatitidis, Cryptococcus neoformans*, and *Aspergillus fumigatus*. In certain aspects the pathogen is an influenza virus. In a further aspect the influenza virus is influenza A virus. In certain aspects the method can further comprise administering an antimicrobial (antiviral, antibiotic, or antifungal) drug in conjunction with the anti-S100A9 antibody.

In further aspects an antiviral drug is an amantadine, a neuraminidase inhibitor (e.g., oseltamivir and zanamivir), ribavirin, and/or palivizumab. In certain embodiments, the second therapeutic agent is selected from the group consisting of amantadine, oseltamivir, and zanamivir.

In certain aspects, the anti-S100A9 antibody is administered intratracheally. Intratracheal administration can be in the form of instillation or inhalation of a composition comprising the anti-S100A9 antibody. In certain aspects, the anti-S100A9 antibody is administered via a systemic administration. For example, a systemic administration may be via an intraperitoneal injection or an intravenous injection.

Certain embodiments are directed to methods and compositions comprising neutralizing antibodies to S100A9 to reduce or ameliorate inflammation during a respiratory infection. In certain aspects the infection is an influenza A infection. In certain embodiments the methods and compositions can be used prophylactically in a subject at risk of infection or is susceptible to development of lung disease if infected, for example the elderly or immune suppressed subject.

In another aspect, the infection is a Coronavirus infection. For example. The Coronavirus infection can include SARS CoV-2, MERS-COV, COVID-19, and mutant viral strains arising from COVID-19. In certain embodiments the methods and compositions can be used prophylactically to prevent and/or mitigate effects in a subject at risk of infection or is susceptible to development of lung disease if infected with a Coronavirus (e.g., COVID-19). Subjects include the elderly, obese subjects, diabetics, those with afflicted with preconditions (e.g., cancer patients, sarcoid patients, etc.) as well as immunosuppressed subjects.

Other embodiments of the invention are discussed throughout this application. Any embodiment discussed with respect to one aspect of the invention applies to other aspects of the invention as well and vice versa. Each embodiment described herein is understood to be an embodiment of the invention that is applicable to other aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(FIG. 2A) Primary bone marrow derived macrophages or BMDMs isolated from wild-type (WT), TLR2 knockout (KO), TLR4 KO and TRIF KO mice were infected with IAV (2 MOI). At 24 hours post-infection time-period the medium supernatant was collected to assess levels of S100A9 protein by ELISA. (FIG. 2B) RT-PCR analysis of S100A9 expression in IAV infected WT and TRIF KO BMDMs. (FIG. 2C) BMDMs isolated from WT and TLR3 KO mice were infected with IAV (2 MOI). At indicated post-infection time-periods the medium supernatant was collected to assess levels of S100A9 protein by ELISA. (FIG. 2D) Mouse alveolar macrophage cell-line MH-S was transfected with either control siRNA or DDX21 specific siRNA. At 48 hours post-transfection, cells were infected with IAV (2 MOI). At indicated post-infection time-period RT-PCR analysis was performed to examine expression of DDX21 in IAV infected control and DDX21 silenced cells. (FIG. 2E) MH-S cells transfected with either control siRNA or DDX21 specific siRNA were infected with IAV (2 MOI). At indicated post-infection time-period the medium supernatant was collected to assess levels of S100A9 protein by ELISA. (FIG. 2F) BMDMs isolated from WT and TLR7 KO mice were infected with IAV (2 MOI). At indicated post-infection time-periods the medium supernatant was collected to assess levels of S100A9 protein by ELISA. The values shown in (FIG. 2A), (FIG. 2C), (FIG. 2E) and (FIG. 2F) represent the mean±standard deviation from three independent experiments performed in triplicate. *$p<0.05$ using a Student's t test. Each RT-PCR data (FIG. 2B and FIG. 2D) is a representative of three independent experiments with similar results.

(FIG. 4A) Mouse J774A.1 macrophages were infected with IAV (2 MOI) in the presence of either control IgG (IgG) or anti-S100A9 blocking (neutralizing) antibody (S100A9 Ab). At indicated post-infection time-periods the medium supernatant was collected to assess levels of mouse IL-6 by ELISA. (FIG. 4B) Primary bone marrow derived macrophages (BMDM) isolated from wild-type (WT) and S100A9 knockout (KO) mice were infected with IAV (2 MOI). The medium supernatant was collected to assess levels of mouse IL-6 by ELISA. (FIG. 4C) WT and S100A9 KO BMDM were infected with IAV (2 MOI). At the indicated post-infection time-period, medium supernatant was collected to assess levels of mouse TNF-α (TNF) by ELISA. (FIG. 4D) S100A9 KO BMDMs were infected with IAV (2 MOI) in the presence of purified recombinant mouse S100A9 protein (5 μg/ml). Medium supernatant was collected from infected cells to assess levels of mouse TNF and IL-6 by ELISA. Vehicle control cells (veh) were incubated with HBSS buffer. The values represent the mean±standard deviation from three independent experiments performed in triplicate. *p<0.05 using a Student's t test.

(FIG. 5A) Mouse J774A.1 macrophages were incubated with purified recombinant mouse S100A9 protein (5 μg/ml) for 48 hours and 72 hours. The apoptotic state of these cells was examined by FACS analysis of annexin V and PI stained cells. Apoptosis rate (% apoptosis) was calculated based on number of annexin V positive/PI negative cells (denoting early apoptosis)+number of annexin V positive/PI positive cells (denoting late apoptosis)/total number of cells. (FIG. 5B) Mouse alveolar macrophage MH-S cell-line was incubated with purified S100A9 protein (5 μg/ml) for 48 hours and 72 hours. The apoptotic status was determined as described in (FIG. 5A). (FIG. 5C) Mouse J774A.1 macrophages were infected with IAV (2 MOI) in the presence of either control IgG (IgG) or anti-S100A9 blocking (neutralizing) antibody (S100A9 Ab). At 48 hours post-infection, the apoptotic state of these cells was determined as described in (FIG. 5A). The values (i.e. annexin V and PI staining quantified by FACS) represents mean±standard deviation from three independent experiments, *p<0.05 by Student's t test. Veh; cells incubated with HBSS buffer (vehicle control).

(FIG. 6C) IL-6 production from S100A9 protein treated WT and MyD88 KO BMDMs. (FIG. 6D) BMDM isolated from WT, TLR4 KO and MyD88 KO mice were infected with IAV (2 MOI). At 12 hours and 24 hours post-infection time-period, medium supernatant was collected to assess levels of mouse IL-6 by ELISA. (FIG. 6E) TNF production from IAV infected WT and TLR4 KO BMDMs. The values represent the mean±standard deviation from three independent experiments performed in triplicate, *p<0.05 using a Student's t test. Veh; cells incubated with HBSS buffer (vehicle control).

(FIG. 7A) Primary bone marrow derived macrophages (BMDM) isolated from wild-type (WT) and TLR4 knockout (KO) mice were incubated with purified recombinant mouse S100A9 protein (5 ug/mL) for 72 hours. The apoptotic state of these cells was examined by FACS analysis of annexin V and PI stained cells. Apoptosis rate (% apoptosis) was calculated based on number of annexin V positive/PI negative cells (denoting early apoptosis)+number of annexin V positive/PI positive cells (denoting late apoptosis)/total number of cells. (FIG. 7B) WT and TLR4 KO BMDMs were infected with IAV (1 MOI). At 48 hours post-infection, the apoptotic status was determined as described in (FIG. 7A). (FIG. 7C) IAV infected WT and TLR4 KO cells were subjected to TUNEL assay. TUNEL positive cells were analyzed by image J software. Percent TUNEL positive cells denotes ratio of number of TUNEL positive cells/total number of cells. (FIG. 7D) WT and MyD88 KO BMDMs were infected with IAV (1 MOI). At 48 hours post-infection, the apoptotic status was determined. The values represents mean±standard deviation from three independent experiments, *p<0.05 by Student's t test. Veh; cells incubated with HBSS buffer (vehicle control).

(FIG. 8A) RNA isolated from mock infected and IAV infected ($2\times10^4$ pfu/mouse via intra-tracheal route) mice were subjected to RT-PCR analysis to examine expression of mouse S100A9. The RT-PCR data represents three mice/group (i.e. three mock mice, three mice infected with IAV for 3 days, and three mice infected with IAV for 6 days). The RT-PCR data is a representative of three independent experiments with similar results. (FIG. 8B) Lung homogenate prepared from mock infected and IAV infected ($2\times10^4$ pfu/mouse via intra-tracheal route) mice were subjected to ELISA analysis to determine levels of mS100A9 protein in the lung. (FIG. 8C) Immuno-histochemical analysis of mouse lung tissue sections derived from mock infected and IAV infected mice were stained with mouse S100A9 antibody. Magnification, 200×. One representative example of a total of 3 mice analyzed per group in two independent experiments. (FIG. 8D) Broncho-alveolar lavage fluid (BALF) isolated from mock infected and IAV infected ($2\times10^4$ pfu/mouse via intra-tracheal route) mice were subjected to ELISA analysis to determine levels of S100A9 protein in BALF. The values shown in (FIG. 8B) and (FIG. 8D) represent the mean±standard deviation from three independent experiments performed in triplicate. *p<0.05 using a Student's t test.

(FIG. 9A) Survival of IAV infected ($1\times10^5$ pfu/mouse via intra-tracheal route) mice administered with either control IgG (IgG) or anti-S100A9 blocking (neutralizing) antibody (S100A9 Ab) (24 hours prior to IAV inoculation, 2 mg of antibody/mouse administered via i.p route). The data represents values from two independent experiments performed with 5 mice/group for each experiment (total 10 mice/group from two experiments); *p=0.03. (FIG. 9B) Hematoxylin and eosin (H&E) staining of lung sections from mock infected or IAV infected mice ($3\times10^4$ pfu/mouse via intra-tracheal route) administered with either control IgG (IgG) or S100A9 Ab (24 hours prior to IAV inoculation, 2 mg of antibody/mouse was administered via i.p route). Magnification, ×10. (FIG. 9C) Mice were administered with purified recombinant mouse S100A9 protein (15 µg/mouse) via intra-tracheal route. At 8 hours post-administration, levels of mouse TNF-α in the lung was assessed by performing ELISA analysis with lung homogenate. (FIG. 9D) Lung homogenate prepared from mock infected and IAV infected (2×10$^4$ pfu/mouse via intra-tracheal route) mice administered with either control IgG (IgG) or anti-S100A9 blocking (neutralizing) antibody (S100A9 Ab) (24 hours prior to IAV inoculation, 2 mg of antibody/mouse administered via i.p route) were subjected to ELISA analysis to determine levels of mouse TNF-α in the lung. (FIG. 9E) For ex-vivo experiment, broncho-alveolar lavage fluid (BALF) was collected (at 3 days post-infection) from IAV infected mice (2×10$^4$ pfu/mouse via intra-tracheal route) mice administered with either control IgG (IgG) or anti-S100A9 blocking (neutralizing) antibody (S100A9 Ab) (24 hours prior to IAV inoculation, 2 mg of antibody/mouse administered via i.p route). The BALF cells were isolated and plated in 48-well plate. After 2 hours and 4 hours, the medium supernatant was analyzed for mouse TNF-α (TNF) and mouse IL-6 by ELISA. Values shown in (FIG. 9C), (FIG. 9D) and (FIG. 9E) represent the mean±standard deviation from three independent experiments performed in triplicate. *p<0.05 using a Student's t test. Veh; HBSS buffer diluted in PBS (vehicle control).

(FIG. 10A) Lung sections were prepared (at 3 days post-infection) from IAV infected (2×10$^4$ pfu/mouse via intra-tracheal route) mice administered with either control IgG (IgG) or anti-S100A9 blocking (neutralizing) antibody (S100A9 Ab) (24 hours prior to IAV inoculation, 2 mg of antibody/mouse administered via i.p route). For each experimental group lung sections were prepared from three control IgG treated mice (+IAV) and three S100A9 Ab treated mice (+IAV). The lung sections were used for TUNEL staining. Image J software was used to calculate TUNEL-positive areas (representing apoptosis) in the lung sections as detailed in the methods section. The data is presented as percent apoptotic area. The percent apoptotic area was calculated from nine areas/lung section as detailed in the methods section. The values were compiled to calculate the percent apoptotic area in IAV infected IgG treated mice vs. IAV infected S100A9 Ab treated mice, *p=0.0164 by Student's t test. (FIG. 10B) A representative TUNEL staining of lung sections from IAV infected mice administered with either IgG or S100A9 Ab. The apoptotic nuclei (representing apoptosis) are indicated with red arrows. (FIG. 10C) A schematic model depicting the role of extracellular S100A9 and DDX21/TRIF/S100A9/TLR4/MyD88 signaling network in exaggerating lung disease during IAV infection. PM, plasma membrane; NM, nuclear membrane.

DESCRIPTION

Figure 1A:
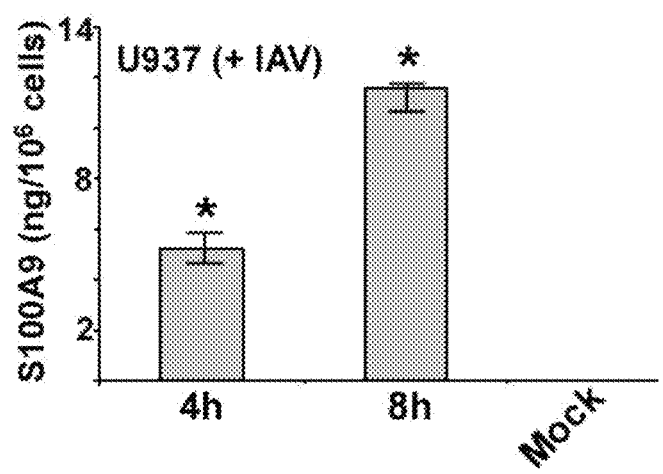
FIGS. 1A-1D. Production of S100A9 from IAV infected macrophages. U937 cells (FIG. 1A), J774A.1 cells (FIG. 1B), primary bone marrow derived macrophages or BMDM (FIG. 1C) and primary mouse alveolar macrophages (FIG. 1D) were infected with IAV. U937 cells were infected at 1 MOI, whereas J774A.1, BMDM and primary alvelolar macrophages were infected at 2 MOI. At indicated post-infection time-periods the medium supernatant was collected to assess levels of S100A9 protein by ELISA. The values shown represent the mean±standard deviation from three independent experiments performed in triplicate. *$p<0.05$ using a Student's t test.

Influenza, commonly known as "the flu", is an infectious disease caused by the influenza virus. Symptoms can be mild to severe. The most common symptoms include: a high fever, runny nose, sore throat, muscle pains, headache, coughing, and feeling tired. These symptoms typically begin two days after exposure to the virus and most last less than a week. The cough; however, may last for more than two weeks. In children there may be nausea and vomiting but these are not common in adults. Nausea and vomiting occur more commonly in the unrelated infection gastroenteritis, which is sometimes inaccurately referred to as "stomach flu" or "24-hour flu". Complications of influenza may include viral pneumonia, secondary bacterial pneumonia, sinus infections, and worsening of previous health problems such as asthma or heart failure. In the context of this application influenza is used as an example of an inflammation inducing microbe. Embodiments are directed to pathogens that induce a similar response mediated by or including the S100A9 protein.

Additional inflammation associated airway diseases are also contemplated to be within the scope of the present disclosure. For example, airway diseases commonly associated with an inflammatory component include pneumonia, bronchiolitis, chronic obstructive pulmonary disease (COPD), and asthma. The therapeutic compositions described herein are also applicable to treatment of an inflammation associated airway disease. Furthermore, the recent spread of COVID-19 and the aforementioned SARS-CoV-2 may result in disease states such as pneumonia, which manifests due to exaggerated airway inflammation. Pneumonia causes severe lung tissue damage, fluid accumulation (edema) and death in affected patients.

Influenza viruses are RNA viruses that make up three of the five genera of the family Orthomyxoviridae: Influenza virus A, Influenza virus B, and Influenza virus C. These viruses are only distantly related to the human parainfluenza viruses, which are RNA viruses belonging to the paramyxovirus family that are a common cause of respiratory infections in children such as croup, but can also cause a disease similar to influenza in adults.

Influenza virus A has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1, H2N2, H3N2, H5N1, H7N7, H1N2, H9N2, H7N2, H7N3, H10N7, and H7N9.

The Influenza virus B genus has one species, influenza B virus. Influenza B almost exclusively infects humans and is less common than influenza A. This type of influenza mutates at a rate 2-3 times slower than type A and consequently is less genetically diverse, with only one influenza B serotype.

The Influenza virus C genus has one species, influenza C virus, which infects humans, dogs and pigs, sometimes causing both severe illness and local epidemics. However, influenza C is less common than the other types and usually only causes mild disease in children.

Coronaviruses are named for the crown-like spikes on their surface. There are four main sub-groupings of coronaviruses, known as alpha, beta, gamma, and delta. Human coronaviruses were first identified in the mid-1960s. People around the world are commonly infected with certain human coronaviruses, such as 229E (alpha coronavirus), NL63 (alpha coronavirus), OC43 (beta coronavirus), and HKU1 (beta coronavirus). In addition, coronaviruses that infect animals can evolve to infect humans, thus becoming a novel human coronavirus. Three recent examples of novel human coronavirus include 2019-nCoV, SARS-CoV, and MERS-CoV.

Pathogen-associated molecular patterns (PAMPs) trigger host immune response by activating pattern recognition receptors like toll-like receptors (TLRs). However, the mechanism whereby several pathogens, including viruses, activate TLRs via a non-PAMP mechanism is unclear. Endogenous "inflammatory mediators" called damage-associated molecular patterns (DAMPs) have been implicated in regulating immune response and inflammation. However, the role of DAMPs in inflammation/immunity during virus infection has not been studied. We have identified a DAMP molecule, S100A9 (also known as Calgranulin B or MRP-14), as an endogenous non-PAMP activator of TLR signaling during influenza A virus (IAV) infection. S100A9 was released from undamaged IAV-infected cells and extracellular S100A9 acted as a critical host-derived molecular pattern to regulate inflammatory response outcome and disease during infection by exaggerating pro-inflammatory response, cell-death and virus pathogenesis. Genetic studies showed that the DDX21-TRIF signaling pathway is required for S100A9 gene expression/production during infection. Furthermore, the inflammatory activity of extracellular S100A9 was mediated by activation of the TLR4-MyD88 pathway. Our studies have thus, underscored the role of a DAMP molecule (i.e. extracellular S100A9) in regulating virus-associated inflammation and uncovered a previously unknown function of the DDX21-TRIF-S100A9-TLR4-MyD88 signaling network in regulating inflammation during infection.

Protein S100A9 is also known as migration inhibitory factor-related protein 14 (MRP-14) or calgranulin-B and is a protein that in humans is encoded by the S100A9 gene. S100A9 is a member of the S100 family of proteins containing two EF hand calcium-binding motifs. S100 proteins are localized in the cytoplasm and/or nucleus of a wide range of cells, and are involved in the regulation of a number of cellular processes such as cell cycle progression and differentiation. S100 genes include at least 13 members that are located as a cluster on chromosome 1q21. Human S100A9 (Unipro accession P06702) has an amino acid sequence of (SEQ ID NO: 15)
MTCKMSQLERNIETIINTFHQYSVKLGHPDTLNQGEFKELVRKDLQNFLK
KENKNEKVIEHIMEDLDTNADKQLSFEEFIMLMARLTWASHEKMHEGDEG
PGHHHKPGLGEGTP.

I. THERAPEUTIC COMPOSITIONS

Embodiments described herein are directed to a composition comprising an antibody that binds and neutralizes S100A9 ability to induce inflammation. Certain aspects are directed an antibody fragment or antibody conjugate, sufficient to treat or ameliorate pathogen-induced inflammation or a complication thereof in a subject or a disease or complication associated with a pathogen infection in a subject wherein said antibody or antibody fragment or antibody conjugate binds immunospecifically to a S100A9. In certain aspects the pathogen is a virus. In certain aspects the virus is a respiratory virus, such as influenza. In a further aspect the pathogen is influenza A. Methods to determine influenza A viral strains are well known to persons skilled in the art. Therefore, influenza A viral strain variants (including, for example, future mutations of influenza A strains and yet undetermined influenza A viral strains) are within the scope of the instant disclosure.

As used herein, the term "amount" refers to a concentration of antibody or antibody fragment or antibody conjugate as determined by any means known to a skilled artisan, including weight of antibody, antibody titer of a unit dose, or a concentration of a unit dose of an antibody or antibody fragment or antibody conjugate. Preferably, an amount of an antibody or antibody fragment or antibody conjugate sufficient to treat or prevent pathogen-induced inflammation or a complication thereof in a subject or diseases associated with a pathogen infection. In certain embodiments a subject is administered an amount of antibody or antibody fragment that is sufficient to neutralize S100A9 activity as is it relates to inflammation in an infected subject.

By "neutralize" is meant that the antibody or antibody fragment or antibody conjugate blocks the inflammation inducing capacity of S100A9. The precise amount of the antibody or antibody fragment or antibody conjugate will vary depending on the specific activity of the antibody or fragment and/or the purpose for which the composition is to be used. Accordingly, this term is not to be construed to limit the invention to a specific quantity, e.g., weight or concentration. Methods for assessing efficacy of any amount of an antibody or antibody fragment or antibody conjugate for treating or preventing virally induced inflammation or complication thereof in a subject or a diseases associated with an infection will be apparent to the skilled artisan from the disclosure herein.

The term "antibody" means any protein or protein fragment having a binding domain with the required specificity and/or affinity for an epitope, including an immunoglobulin, antibody fragment, e.g., VH, VL, Fab, Fab', F(ab)2, Fv, etc. Preferred "antibodies" within this definition include intact polyclonal or monoclonal antibodies, an immunoglobulin (IgA, IgD, IgG, IgM, IgE) fraction, a chimeric antibody, a humanized antibody, an antibody fragment, or an immunoglobulin binding domain, whether natural or synthetic, and conjugates comprising same. Chimeric molecules including an immunoglobulin binding domain, or equivalent, fused to another polypeptide are also included within the meaning of the term "antibody" as used herein.

Anti-S100A9 antibodies, antibody fragments and antibody conjugates are reactive with an epitope of the S100A9 protein. For example, an anti-S100A9 antibody may be a blocking antibody or a neutralizing antibody. In certain aspects, antibodies are immunoglobulin fractions or monoclonal antibodies or recombinant antibodies or humanized versions thereof.

By "humanized antibody" is meant an antibody, antibody fragment or antibody conjugate comprising variable region framework residues substantially from, for example, a human antibody (termed an acceptor antibody) and complementarity determining regions substantially from, for example, a mouse-antibody, (referred to as the donor immunoglobulin). Constant region(s), if present, is(are) substantially or entirely from a human immunoglobulin. The human variable domains are usually chosen from human antibodies whose framework sequences exhibit a high degree of sequence identity with a murine variable region domain from which the CDRs were derived. The heavy and light chain variable region framework residues can be derived from the same or different human antibody sequences. The human antibody sequences can be the sequences of naturally-occurring human antibodies or can be consensus sequences of several human antibodies.

As used herein, the term "treat" or variations thereof such as "treatment" shall be taken to mean a treatment that ameliorates, reduces, or inhibits inflammation caused by a viral infection, or prevents or reduces the severity of one or more symptoms of a viral infection. It is to be understood that such treatment therefore includes the prophylaxis of a viral infection in so far as it prevents or reduces symptom development in an infected individual and/or prevents development of a complication thereof.

As used herein, the term "prophylactic treatment" refers to either preventing or inhibiting the development of a clinical condition or disorder or delaying the onset of a pre-clinically evident stage of a clinical condition or disorder. The term is to be understood as meaning that the compositions according to the present invention can be applied before symptoms of the infection are manifest. The compounds according to the present invention can, for example, be used in a prophylactic treatment.

The composition comprising an antibody, antibody fragment or antibody conjugate that binds S100A9 as described herein is useful for treating an infection or complication thereof in a human or other mammalian subject or for treating a disease associated with infection of the respiratory system in a human or other mammalian subject. Preferably, the composition is for the treatment of humans.

Certain aspects provide a pharmaceutical composition comprising a dose of one or more antibodies, antibody fragments, or antibody conjugates as described herein and a pharmaceutically acceptable carrier or excipient. Such compositions can be formulated for intratracheal or intranasal, delivery. Unit doses of antibody, antibody fragment, or antibody conjugate can comprise from about 0.1 m immunoglobulin per kilogram body weight to about 100 mg immunoglobulin per kilogram body weight, from about 0.1 m immunoglobulin per kilogram body weight to about 20 mg immunoglobulin per kilogram body weight, from about 0.1 m immunoglobulin per kilogram body weight to about 10 mg immunoglobulin per kilogram body weight, or from about 0.1 m immunoglobulin per kilogram body weight to about 1.0 mg immunoglobulin per kilogram body weight. Suitable carriers and excipients will vary according to the mode of administration and storage requirements of a composition comprising an antibody, antibody fragment, or antibody conjugate and are described herein.

As used herein, the term "suitable carrier or excipient" shall be taken to mean a compound or mixture thereof that is suitable for use in a composition for administration to a subject for the treatment of viral infection or complication thereof in a subject or a disease or complication associated with a viral infection in a subject. For example, a suitable carrier or excipient for use in a pharmaceutical composition for injection into a subject will generally not cause an adverse response in a subject.

A carrier or excipient useful in the pharmaceutical composition will generally not inhibit to any significant degree a relevant biological activity of an antibody, antibody fragment, or antibody conjugate as described according to any embodiment hereof, e.g., the carrier or excipient will not significantly inhibit the ability of an antibody, fragment, or conjugate to bind to and neutralize S100A9. In certain aspects the carrier or excipient may include an antimicrobial compound.

Embodiments are directed to a method of treating or ameliorating inflammation due to an infection (e.g., an infection of the respiratory system) in a human or other mammalian subject. The method can comprise administering to a subject having an infection or suspected of having an infection or at risk of having an infection a composition as described herein. The composition can be administered in an amount effective to prevent viral induced inflammation in a subject.

In an alternative embodiment, the present invention also provides a method of preventing, ameliorating or treating a disease or complication associated with an infection or respiratory infection of a human or other mammalian subject. The method can comprise administering to the subject a composition as described herein in an amount effective to reduce the severity of one or more disease symptoms or to prevent onset of one or more diseases arising from the infection. In certain aspects, a method of treating a respiratory virus infection in a subject is provided. The method comprises the step of administering an anti-S100A9 antibody to the subject in need of thereof. In some embodiments, the respiratory virus is RSV. In other embodiments, the administration of the anti-S100A9 antibody reduces RSV infection in the respiratory tract of the subject via a decrease in viral titer.

A further embodiment is directed a method of neutralizing the activity of S100A9 in the lungs of a subject exposed to a pathogen. The method can comprise administering to a subject infected with a pathogen a composition as described herein in an amount effective to reduce or neutralize S100A9 activity in the lung of the subject.

In certain embodiments, the therapeutic antibody, antibody fragment or immunogenic moiety of an antibody conjugate is human or humanized, e.g., an antibody wherein the human content of the antibody is maximized while causing little or no loss of binding affinity attributable to the variable region of an antibody produced by a non-human antibody.

As discussed supra antibody fragments are contemplated. The term "antibody fragment" refers to a portion of a full-length antibody, generally the antigen binding or variable region. Examples of antibody fragments include Fab, Fab', F(ab')2 and Fv fragments.

"Single-chain Fv" or "scFv" antibody fragments comprise the VH and VL domains of an antibody, wherein these domains are present in a single polypeptide chain. Generally, the Fv polypeptide further comprises a polypeptide linker between the VH and VL domains which enables the scFv to form the desired structure for antigen binding.

The compositions and methods of the present invention may be used in the context of a number of therapeutic or prophylactic applications. In order to increase the effectiveness of a treatment with the compositions of the present invention or to augment the protection of another therapy (a second therapeutic agent), e.g., antimicrobial therapy, it may be desirable to combine these compositions and methods with other agents and methods effective in the treatment, reduction of risk of infection, or prevention of diseases and pathologic conditions, for example, anti-bacterial, anti-viral, and/or anti-fungal treatments.

In certain aspects of the invention an anti-viral agent may be used in combination with a therapeutic composition described herein. Anti-viral agents include, but are not limited to abacavir; acemannan; acyclovir; acyclovir sodium; adefovir; alovudine; alvircept sudotox; amantadine hydrochloride; amprenavir; aranotin; arildone; atevirdine mesylate; avridine; cidofovir; cipamfylline; cytarabine hydrochloride; delavirdine mesylate; desciclovir; didanosine; disoxaril; edoxudine; efavirenz; enviradene; enviroxime; famciclovir; famotine hydrochloride; fiacitabine; fialuridine; fosarilate; trisodium phosphonoformate; fosfonet sodium; ganciclovir; ganciclovir sodium; idoxuridine; indinavir; kethoxal; lamivudine; lobucavir; memotine hydrochloride; methisazone; nelfinavir; nevirapine; palivizumab; penciclovir; pirodavir; ribavirin; rimantadine hydrochloride; ritonavir; saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zidovudine; zinviroxime, interferon, cyclovir, alpha-interferon, and/or beta globulin. In certain aspects, other antibodies against viral proteins or cellular factors may be used in combination with a therapeutic composition described herein.

Examples of anti-bacterials include, but are not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams,), β-lactamase inhibitors, vancomycin, aminoglycosides and spectinomycin, tetracyclines, chloramphenicol, erythromycin, lincomycin, clindamycin, rifampin, metronidazole, polymyxins, sulfonamides and trimethoprim, and quinolines. Anti-bacterials also include, but are not limited to: Acedapsone, Acetosulfone Sodium, Alamecin, Alexidine, Amdinocillin, Amdinocillin Pivoxil, Amicycline, Amifloxacin, Amifloxacin Mesylate, Amikacin, Amikacin Sulfate, Aminosalicylic acid, Aminosalicylate sodium, Amoxicillin, Amphomycin, Ampicillin, Ampicillin Sodium, Apalcillin Sodium, Apramycin, Aspartocin, Astromicin Sulfate, Avilamycin, Avoparcin, Azithromycin, Azlocillin, Azlocillin Sodium, Bacampicillin Hydrochloride, Bacitracin, Bacitracin Methylene Disalicylate, Bacitracin Zinc, Bambermycins, Benzoylpas Calcium, Berythromycin, Betamicin Sulfate, Biapenem, Biniramycin, Biphenamine Hydrochloride, Bispyrithione Magsulfex, Butikacin, Butirosin Sulfate, Capreomycin Sulfate, Carbadox, Carbenicillin Disodium, Carbenicillin Indanyl Sodium, Carbenicillin Phenyl Sodium, Carbenicillin Potassium, Carumonam Sodium, Cefaclor, Cefadroxil, Cefamandole, Cefamandole Nafate, Cefamandole Sodium, Cefaparole, Cefatrizine, Cefazaflur Sodium, Cefazolin, Cefazolin Sodium, Cefbuperazone, Cefdinir, Cefepime, Cefepime Hydrochloride, Cefetecol, Cefixime, Cefmenoxime Hydrochloride, Cefmetazole, Cefmetazole Sodium, Cefonicid Monosodium, Cefonicid Sodium, Cefoperazone Sodium, Ceforanide, Cefotaxime Sodium, Cefotetan, Cefotetan Disodium, Cefotiam Hydrochloride, Cefoxitin, Cefoxitin Sodium, Cefpimizole, Cefpimizole Sodium, Cefpiramide, Cefpiramide Sodium, Cefpirome Sulfate, Cefpodoxime Proxetil, Cefprozil, Cefroxadine, Cefsulodin Sodium, Ceftazidime, Ceftibuten, Ceftizoxime Sodium, Ceftriaxone Sodium, Cefuroxime, Cefuroxime Axetil, Cefuroxime Pivoxetil, Cefuroxime Sodium, Cephacetrile Sodium, Cephalexin, Cephalexii Hydrochloride, Cephaloglycini, Cephaloridine, Cephalothin Sodium, Cephapirin Sodium, Cephradine, Cetocycline Hydrochloride, Cetophenicol, Chloramphenicol, Cliloramphenicol Palmitate, Chloramphenicol Pantotheniate Complex, Chloramphenicol Sodium Succinate, Chlorhexidine Phosphanilate, Chloroxylenol, Chlortetracycline Bisulfate, Chlortetracycline Hydrochloride, Cinoxacin, Ciprofloxacin, Ciprofloxacin Hydrochloride, Cirolemycin, Clarithromycin, Clinafloxacin Hydrochloride, Clildamycin, Clindamycin Hydrochloride, Clindamycin Palmitate Hydrochloride, Clindamycin Phosphate, Clofazimine, Cloxacillin Benzathine, Cloxacillin Sodium, Cloxyquin, Colistimethate Sodium, Colistin Sulfate, Coumermycin, Coumermycin Sodium, Cyclacillin, Cycloserine, Dalfopristin, Dapsone, Daptomycin, Demeclocycine, Demeclocycine Hydrochloride, Demecycline, Denofungin, Diaveridine, Dicloxacillin, Dicloxacillin Sodium, Dihydrostreptomycin Sulfate, Dipyrithione, Dirithromycin, Doxycycline, Doxycycline Calcium, Doxycycline Fosfatex, Doxycycline Hyclate, Droxacin Sodium, Enoxacin, Epicillin, Epitetracycline Hydrochloride, Erythromycin, Erythromycin Acistrate, Erythromycin Estolate, Erythromycin Ethylsuccinate, Erythromycin Gluceptate, Erythromycin Lactobionate, Erythromycin Propionate, Erythromycin Stearate, Ethambutol Hydrochloride, Ethionamide, Fleroxacin, Floxacillin, Fludalanine, Flumequine, Fosfomycin, Fosfomycin Tromethamine, Fumoxicillin, Furazolium Chloride, Furazolium Tartrate, Fusidate Sodium, Fusidic Acid, Gentamicin Sulfate, Gloximonam, Gramicidin, Haloprogin, Hetacillin, Hetacillin Potassium, Hexedine, Ibafloxacin, Imipenem, Isoconazole, Isepamicin, Isoniazid, Josamycin, Kanamycin Sulfate, Kitasamycin, Levofuraltadone, Levopropylcillin Potassium, Lexithromycin, Lincomycin, Lincomycin Hydrochloride, Lomefloxacin, Lomefloxacin Hydrochloride, Lomefloxacin Mesylate, Loracarbef, Mafenide, Meclocycline, Meclocycline Sulfosalicylate, Megalomicin Potassium Phosphate, Mequidox, Meropenem, Methacycline, Methacycline Hydrochloride, Methenamine, Methenamine Hippurate, Methenamine Mandelate, Methicillin Sodium, Metioprim, Metronidazole Hydrochloride, Metronidazole Phosphate, Mezlocillin, Mezlocillin Sodium, Minocycline, Minocycline Hydrochloride, Mirincamycin Hydrochloride, Monensin, Monensin Sodium, Nafcillin Sodium, Nalidixate Sodium, Nalidixic Acid, Natamycin, Nebramycin, Neomycin Palmitate, Neomycin Sulfate, Neomycin Undecylenate, Netilmicin Sulfate, Neutramycin, Nifuradene, Nifuraldezone, Nifuratel, Nifuratrone, Nifurdazil, Nifurimide, Nifuirpirinol, Nifurquinazol, Nifurthiazole, Nitrocycline, Nitrofurantoin, Nitromide, Norfloxacin, Novobiocin Sodium, Ofloxacin, Ormetoprim, Oxacillin Sodium, Oximonam, Oximonam Sodium, Oxolinic Acid, Oxytetracycline, Oxytetracycline Calcium, Oxytetracycline Hydrochloride, Paldimycin, Parachlorophenol, Paulomycin, Pefloxacin, Pefloxacin Mesylate, Penamecillin, Penicillin G Benzathine, Penicillin G Potassium, Penicillin G Procaine, Penicillin G Sodium, Penicillin V, Penicillin V Benzathine, Penicillin V Hydrabamine, Penicillin V Potassium, Pentizidone Sodium, Phenyl Aminosalicylate, Piperacillin Sodium, Pirbenicillin Sodium, Piridicillin Sodium, Pirlimycin Hydrochloride, Pivampicillin Hydrochloride, Pivampicillin Pamoate, Pivampicillin Probenate, Polymyxin B Sulfate, Porfiromycin, Propikacin, Pyrazinamide, Pyrithione Zinc, Quindecamine Acetate, Quinupristin, Racephenicol, Ramoplanin, Ranimycin, Relomycin, Repromicin, Rifabutin, Rifametane, Rifamexil, Rifamide, Rifampin, Rifapentine, Rifaximin, Rolitetracycline, Rolitetracycline Nitrate, Rosaramicin, Rosaramicin Butyrate, Rosaramicin Propionate, Rosaramicin Sodium Phosphate, Rosaramicin Stearate, Rosoxacin, Roxarsone, Roxithromycin, Sancycline, Sanfetrinem Sodium, Sarmoxicillin, Sarpicillin, Scopafungin, Sisomicin, Sisomicin Sulfate, Sparfloxacin, Spectinomycin Hydrochloride, Spiramycin, Stallimycin Hydrochloride, Steffimycin, Streptomycin Sulfate, Streptonicozid, Sulfabenz, Sulfabenzamide, Sulfacetamide, Sulfacetamide Sodium, Sulfacytine, Sulfadiazine, Sulfadiazine Sodium, Sulfadoxine, Sulfalene, Sulfamerazine, Sulfameter, Sulfamethazine, Sulfamethizole, Sulfamethoxazole, Sulfamonomethoxine, Sulfamoxole, Sulfanilate Zinc, Sulfanitran, Sulfas alazine, Sulfasomizole, Sulfathiazole, Sulfazamet, Sulfisoxazole, Sulfisoxazole Acetyl, Sulfisoxazole Diolamine, Sulfomyxin, Sulopenem, Sultamicillin, Suncillin Sodium, Talampicillin Hydrochloride, Teicoplanin, Temafloxacin Hydrochloride, Temocillin, Tetracycline, Tetracycline Hydrochloride, Tetracycline Phosphate Complex, Tetroxoprim, Thiamphenicol, Thiphencillin Potassium, Ticarcillin Cresyl Sodium, Ticarcillin Disodium, Ticarcillin Monosodium, Ticlatone, Tiodonium Chloride, Tobramycin, Tobramycin Sulfate, Tosufloxacin, Trimethoprim, Trimethoprim Sulfate, Trisulfapyrimidines, Troleandomycin, Trospectomycin Sulfate, Tyrothricin, Vancomycin, Vancomycin Hydrochloride, Virginiamycin, and/or Zorbamycin.

Anti-fungal agents include, but are not limited to, azoles, imidazoles, polyenes, posaconazole, fluconazole, itraconazole, amphotericin B, 5-fluorocytosine, miconazole, ketoconazole, Myambutol (Ethambutol Hydrochloride), Dapsone (4,4'-diaminodiphenylsulfone), Paser Granules (aminosalicylic acid granules), rifapentine, Pyrazinamide, Isoniazid, Rifadin IV, Rifampin, Pyrazinamide, Streptomycin Sulfate and Trecator-SC (Ethionamide) and/or voriconazole (Vfend™).

II. PHARMACEUTICAL COMPOSITIONS

Certain aspects include pharmaceutical compositions comprising a therapeutic antibody or antibody fragment. In a further aspect the composition can include other active molecules and one or more pharmaceutically acceptable carriers and/or diluents. The active ingredients of a pharmaceutical composition comprising an antibody can exhibit antiviral activity. For example, from about 0.1 mg to about 100 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by delivery to the respiratory system (e.g., intratracheal or intranasal administration). Depending on the route of administration, the active ingredients which comprise an antibody or antibody fragment may be required to be coated in a material to protect said ingredients from the action of enzymes, acids and other natural conditions which may inactivate said ingredients.

Pulmonary/respiratory drug delivery can be implemented by different approaches, including liquid nebulizers, aerosol-based metered dose inhalers (MDI's), sprayers, dry powder dispersion devices and the like. Such methods and compositions are well known to those of skill in the art, as indicated by U.S. Pat. Nos. 6,797,258, 6,794,357, 6,737,045, and 6,488,953, all of which are incorporated by reference. According to the invention, at least one pharmaceutical composition can be delivered by any of a variety of inhalation or nasal devices known in the art for administration of a therapeutic agent by inhalation. Other devices suitable for directing pulmonary or nasal administration are also known in the art. Typically, for pulmonary administration, at least one pharmaceutical composition is delivered in a particle size effective for reaching the lower airways of the lung or sinuses. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), or the like.

All such inhalation devices can be used for the administration of a pharmaceutical composition in an aerosol. Such aerosols may comprise either solutions (both aqueous and non aqueous) or solid particles. Metered dose inhalers typically use a propellant gas and require actuation during inspiration. See, e.g., WO 98/35888; WO 94/16970. Dry powder inhalers use breath-actuation of a mixed powder. See U.S. Pat. Nos. 5,458,135; 4,668,218; PCT publications WO 97/25086; WO 94/08552; WO 94/06498; and European application EP 0237507, each of which is incorporated herein by reference in their entirety. Nebulizers produce aerosols from solutions, while metered dose inhalers, dry powder inhalers, and the like generate small particle aerosols. Suitable formulations for administration include, but are not limited to nasal spray or nasal drops, and may include aqueous or oily solutions of a therapeutic composition as described herein.

A spray comprising a pharmaceutical composition as described herein can be produced by forcing a suspension or solution of a composition through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition as described herein can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the composition creating an aerosol.

It is advantageous to formulate compositions in dosage unit form for ease of administration and uniformity of dosage. "Dosage unit form" as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of a pharmaceutical composition of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in an amount ranging from about 0.1 m to about 100 mg. In the case of compositions containing supplementary active ingredients, the dosages are determined by reference to the usual dose and manner of administration of the said ingredients.

III. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1B:
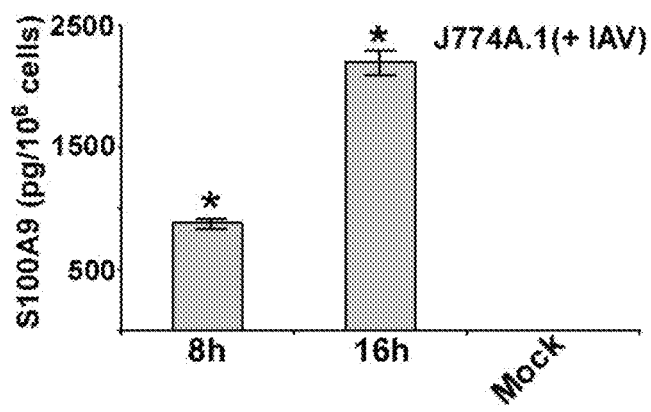
Figure 1C:
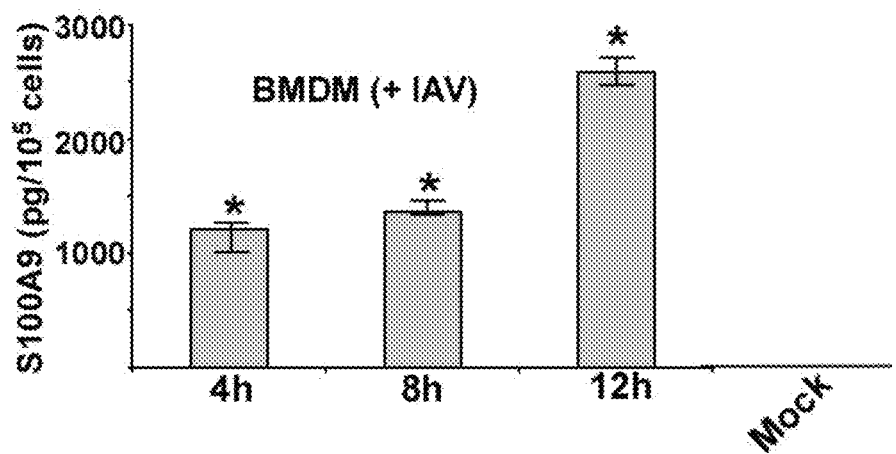
Figure 1D:
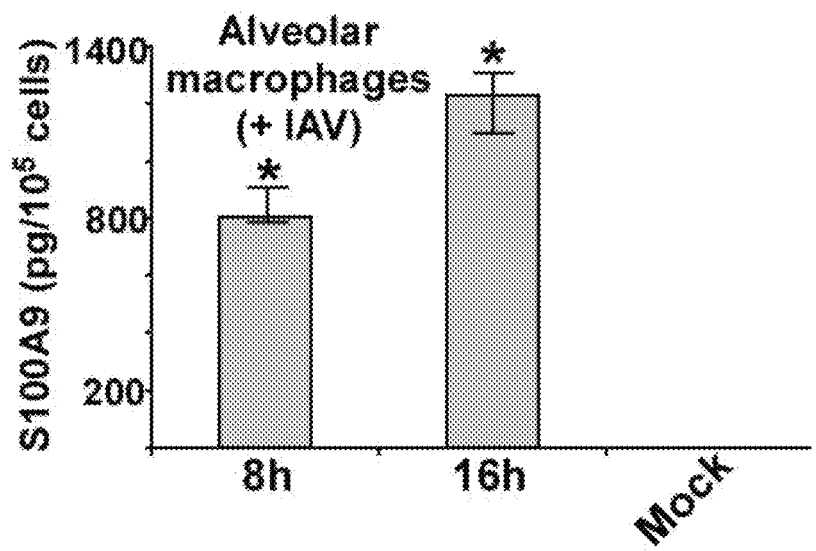

S100A9 secretion from IAV-infected macrophages. Macrophages are essential immune cells that modulate host defense, inflammation, and disease pathogenesis during IAV infection. Macrophages are also the major cytokine- and chemokine-producing cells during IAV infection and thus contribute to lung tissue damage. To investigate whether IAV infection stimulates S100A9 secretion, macrophages were infected with IAV for 4-16 hours. After infection, medium supernatant was collected to assess S100A9 protein levels by ELISA. Following IAV infection both human (U937 cells) (FIG. 1A) and mouse [J774A.1 macrophage cell-line, primary alveolar macrophages, and primary bone marrow-derived macrophages (BMDMs)] macrophages (FIG. 1B-1D) secreted high levels of S100A9. The physiological significance is evident from the ability of primary macrophages (i.e. alveolar macrophages and BMDMs) (FIGS. 1C and 1D) to secrete S100A9 upon IAV infection. Interestingly, S100A9 secretion was detected as early as 4-8 hours postinfection. Release of S100A9 is not due to cell cytotoxicity or damage, since an LDH release cytotoxicity assay showed minimal cytotoxicity in macrophages at 8 and 16 hours postinfection. Similarly, no cell death (apoptosis or necrosis) was observed during the 8-16 hours postinfection period (not shown). These results demonstrated that following IAV infection, S100A9 is released to the extracellular environment from undamaged macrophages.

Figure 2A:
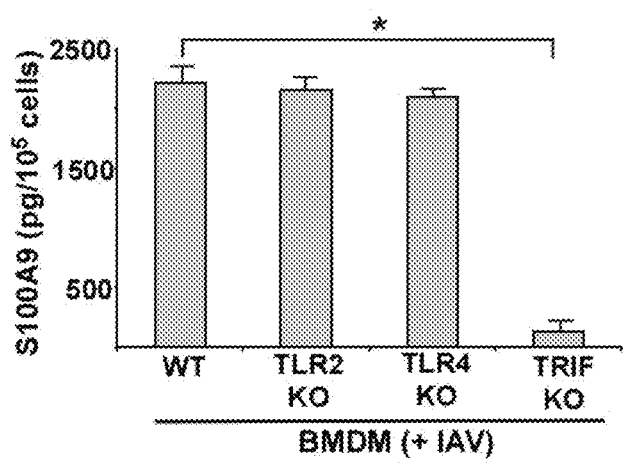
FIGS. 2A-2F. DDX21 and TRIF are required for S100A9 production from IAV infected macrophages.
Figure 2B:
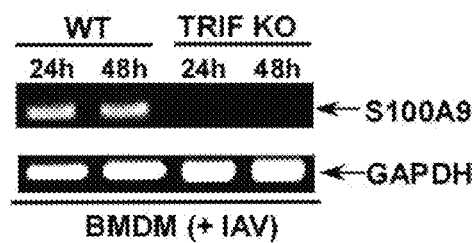
Figure 2C:
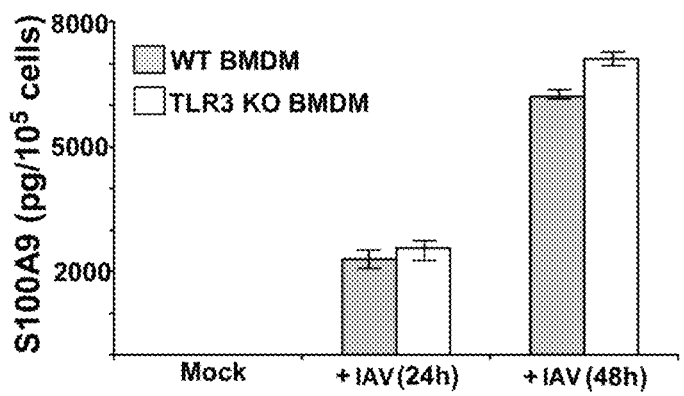

The DDX21/TRIF pathway is required for S100A9 gene expression and secretion during IAV infection. There have been no studies to date on the signaling mechanism that regulates gene expression of S100 family of proteins. The signaling mechanism involved in S100A9 expression was examined. BMDMs derived from wild-type (WT), TLR2 knockout (KO), TLR4 KO, and TRIF KO mice were infected with IAV. At 24 hours postinfection, evaluated S100A9 levels in the medium were evaluated. TLR2 and TLR4 were not involved, since comparable S100A9 secretion was noted in WT and TLR KO BMDMs (FIG. 2A). A similar result was obtained with TRAM KO and TIRAP KO cells (not shown). In contrast, significant reduction in S100A9 secretion was observed in IAV-infected TRIF KO BMDMs (FIG. 2A). RT-PCR analysis showed that loss of S100A9 secretion was caused by the absence of S100A9 mRNA in infected TRIF KO cells (FIG. 2B). Apart from TLR4, which uses TRIF for MyD88-independent signaling, TLR3 also recruits TRIF for TLR3-mediated signal transduction. However, TLR3 is not involved in this process, as shown by the fact that S100A9 secretion was not reduced in TLR3 KO BMDMs (FIG. 2C). These results demonstrated that S100A9 gene induction occurs via the TLR-independent TRIF-dependent pathway.

Recently, DEAD box proteins (also known as DDX protein) having RNA helicase activity has been implicated in innate immunity (Zhang et al. (2011) Immunity 34: 866-878). DDX proteins (e.g. DDX21) can function as cytosolic PRR in mouse dendritic cells (mDCs) to induce type-I interferon during infection (Zhang et al. (2011) Immunity 34: 866-878). Interestingly, DDX signaling was TRIF-dependent and DDX21 interacted with TRIF during signaling (Zhang et al. (2011) Immunity 34: 866-878). Therefore, the inventors examined whether DDX21 has a role in S100A9 expression during IAV infection of macrophages. Since KO animals lacking DDX proteins do not exist, siRNA technology was used to silence DDX21 expression in macrophages.

Figure 2D:
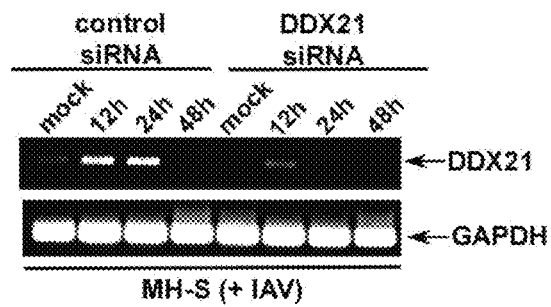
Figure 2E:
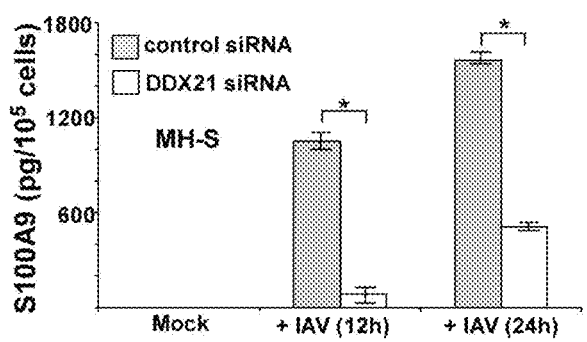
Figure 2F:
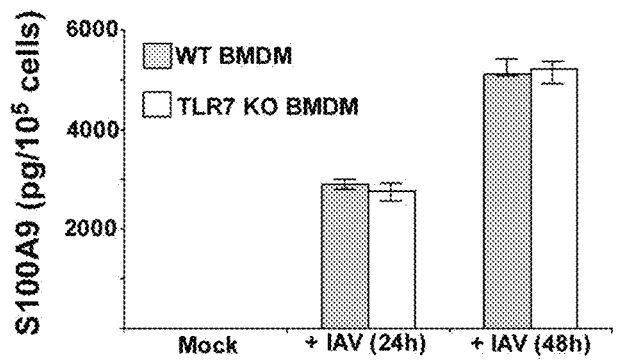
Figure 3A:
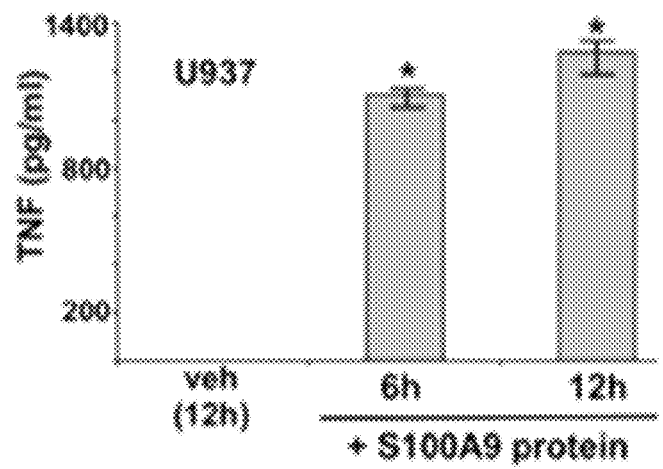
FIGS. 3A-3D. Extracellular S100A9 protein stimulates pro-inflammatory response in macrophages. Human U937 macrophages were incubated with purified recombinant human S100A9 protein (10 μm/ml) for 6 hours and 12 hours. The medium supernatant was collected to assess levels of human TNF-α (TNF) (FIG. 3A) and human IL-6 (FIG. 3B) by ELISA. Mouse J774A.1 macrophages were incubated with purified recombinant mouse S100A9 protein (5 μg/ml) for 6 hours and 12 hours. The medium supernatant was collected to assess levels of mouse TNF (FIG. 3C) and mouse IL-6 (FIG. 3D) by ELISA. The values represent the mean±standard deviation from three independent experiments performed in triplicate. *p<0.05 using a Student's t test. Vehicle control cells (veh) were incubated with HBSS buffer.
Figure 3B:
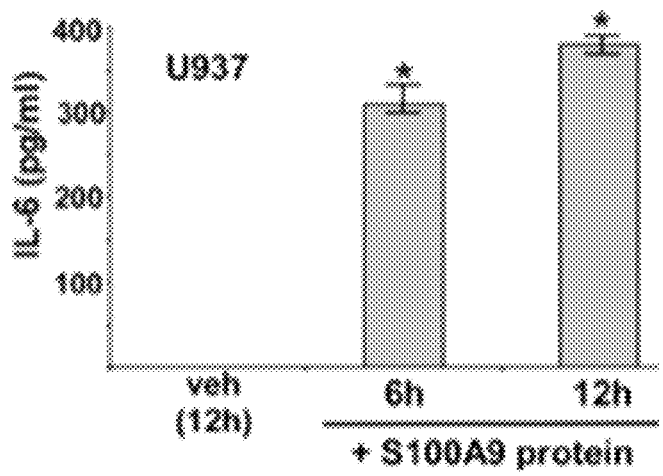
Figure 3C:
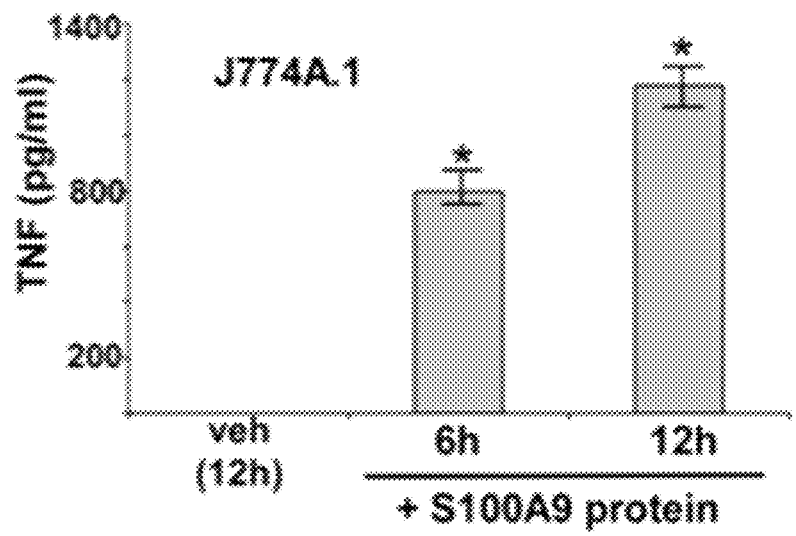
Figure 3D:
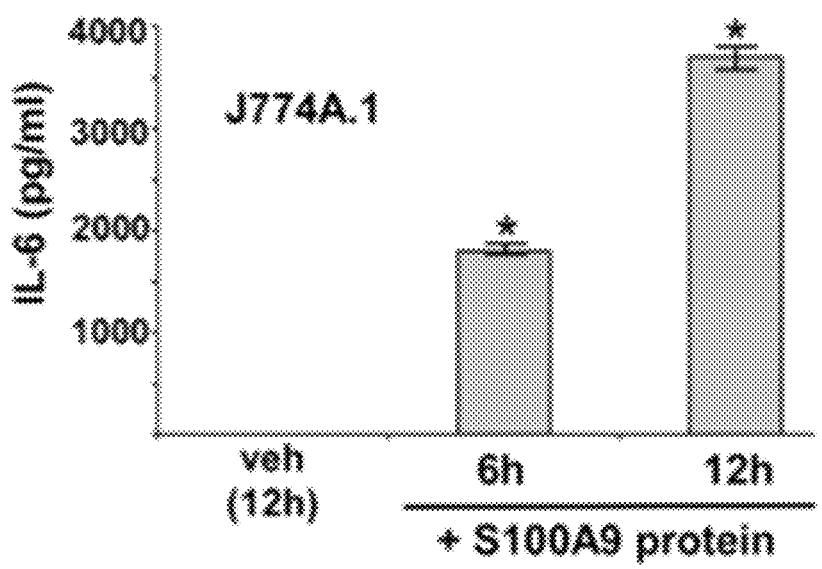

Mouse alveolar macrophages (MH-S cell line) were transfected with DDX21-specific siRNA or control scrambled siRNA, after which these cells were infected with IAV. DDX21 expression was monitored by RT-PCR. Induction of DDX21 expression was observed following IAV infection (FIG. 2D). The silencing efficiency was evident from the loss of DDX21 expression in IAV-infected cells transfected with DDX21-specific siRNA (FIG. 2D). The silenced cells were used to deduce the role of DDX21 in S100A9 gene expression following IAV infection. DDX21 is critical for S100A9 gene expression, since drastic loss of S100A9 mRNA was observed in IAV-infected DDX21 silenced cells. Accordingly, reduced S100A9 mRNA expression in DDX21 silenced cells led to diminished S100A9 secretion following IAV infection of these cells (FIG. 2E). The DDX/TRIF dependent S100A9 expression was independent of virus replication, since IAV hemagglutinin (HA) mRNA levels were similar in DDX21 silenced and TRIF KO cells. Moreover, S100A9 expression (not shown) and production was not significantly altered in IAV infected MyD88 KO and MAVS KO cells, which implicated MyD88 and MAVS independent expression/production of S100A9 during IAV infection. In addition, the inventors failed to observe significant difference in S100A9 expression/production from IAV infected WT vs. TLR7 KO cells (FIG. 2F). It is interesting to note that DDX21 expression was undetected at 48 hours postinfection (FIG. 2D), which co-relates with loss of S100A9 production during that time frame (not shown). This suggests that to maintain homeostasis and to avoid hyper-inflammation cells may negatively regulate DDX21 expression to reduce S100A9 production. These results demonstrated that the DDX21/TRIF pathway is required for S100A9 gene induction and the resulting S100A9 secretion following IAV infection.

Extracellular S100A9 promotes pro-inflammatory response during IAV infection. In the preceding studies, the high levels of S100A9 secretion during infection suggested that secreted extracellular S100A9 may have some role during IAV infection. Therefore, the inventors focused on the role and function of extracellular S100A9 during IAV infection. Earlier studies have shown that the S100A9/S100A8 complex is required for optimal LPS-induced TLR4-dependent TNF-α (TNF) production in bone marrow cells (comprised of undifferentiated monocytes and DCs) (Vogl et al. (2007) Nat Med 13: 1042-1049). However, few studies have shown the pro-inflammatory activity of S100A9 in the absence of S100A8 and LPS. Moreover, it is not known whether S100A9 can launch a pro-inflammatory response in macrophages. Since the studies are focused on the innate responses of IAV-infected macrophages, the inventors investigated whether extracellular addition of purified S100A9 protein (to mimic secreted S100A9) promotes the release of pro-inflammatory cytokines IL-6 and TNF-α (TNF). These pro-inflammatory cytokines are produced early during IAV infection, a period that corresponds with S100A9 secretion kinetics.

Mouse (J774A.1) and human (U937 cells) macrophages were incubated with purified mouse or human S100A9 proteins, respectively for 6-12 hours (FIG. 3). After treatment, medium supernatant was collected to analyze TNF and IL-6 levels by ELISA. S100A9 alone stimulates a pro-inflammatory response in macrophages, as is evident from high levels of TNF (FIGS. 3A and 3C) and IL-6 (FIGS. 3B and 3D) production by macrophages treated with purified S100A9 protein. Both human (FIGS. 3A and 3B) and mouse (FIGS. 3C and 3D) macrophages produced pro-inflammatory cytokines upon incubation with human and mouse S100A9 protein. Interestingly, the response was rapid, since substantial TNF and IL-6 production occurred within 6 hours of treatment with S100A9 protein. RT-PCR analysis showed that production of TNF and IL-6 by S100A9 was due to activation of their corresponding genes. Since the pro-inflammatory activity of purified S100A9 protein could be inhibited by anti-S100A9 blocking (neutralizing) antibody (not shown), the observed response was due to S100A9 protein. Moreover, the effect observed with purified S100A9 protein was not due to LPS contamination. These studies demonstrated that S100A9 functions as an extracellular host factor to launch a pro-inflammatory response in macrophages.

Figure 4A:
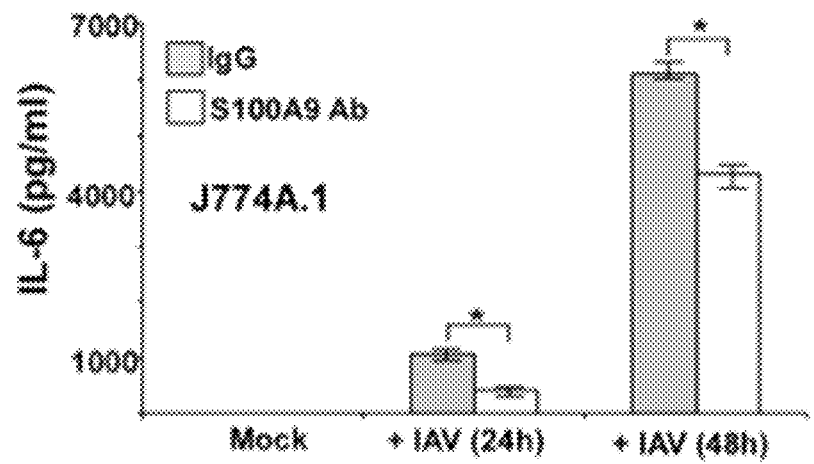
FIGS. 4A-4D. Extracellular S100A9 plays an essential role in inducing pro-inflammatory response during IAV infection of macrophages.

The inventors next examined the role of secreted S100A9 in eliciting a pro-inflammatory response during IAV infection. A blocking antibody against S100A9 was used to neutralize the activity of extracellular (secreted) S100A9. Previously, it was shown that this blocking antibody specifically inhibited the activity of the secreted extracellular form of S100A9 both in vitro and in vivo (Ryckman et al. (2003) J Immunol 170: 3233-3242; Anceriz et al. (2007) Biochem Biophys Res Commun 354: 84-89; Cesaro et al. (2012) PLoS One 7: e45478; Simard et al. (2010) J Leukoc Biot 87: 905-914; Simard et al. (2011) J Immunol 186: 3622-3631; Raquil et al. (2008) J Immunol 180: 3366-3374; Vandal et al. (2003) J Immunol 171: 2602-2609). J774A.1 cells were infected with IAV in the presence of either control antibody (control IgG) or S100A9-specific blocking antibody. At various postinfection time points, IL-6 and TNF levels were examined by ELISA. Extracellular S100A9 plays a key role in inducing the pro-inflammatory response during IAV infection, since significant reduction in IL-6 (FIG. 4A) and TNF levels were observed in infected cells treated with S100A9 blocking antibody. RT-PCR showed that loss of IL-6 and TNF production was due to diminished gene expression (not shown). Similar results were obtained following treatment of IAV-infected primary macrophages (BMDM) with S100A9 blocking antibody. Diminished IL-6 and TNF (not shown) production and expression was observed in infected BMDM treated with S100A9 blocking antibody. The loss of pro-inflammatory response was not due to reduced IAV replication, since IAV HA expression was similar in control antibody and S100A9 blocking antibody treated J774A.1 cells and BMDMs. Thus, extracellular S100A9 modulates pro-inflammatory response independent of IAV replication.

Figure 4B:
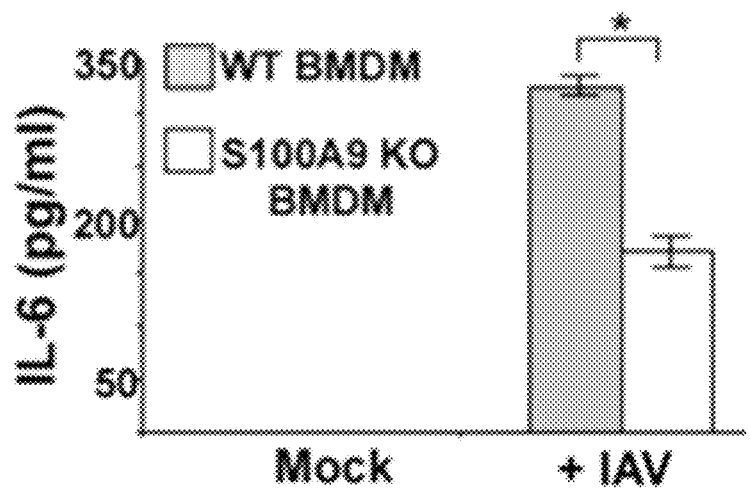
Figure 4C:
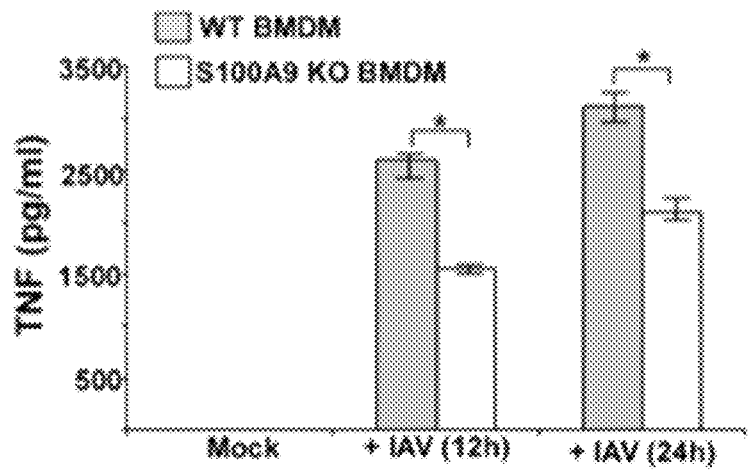
Figure 4D:
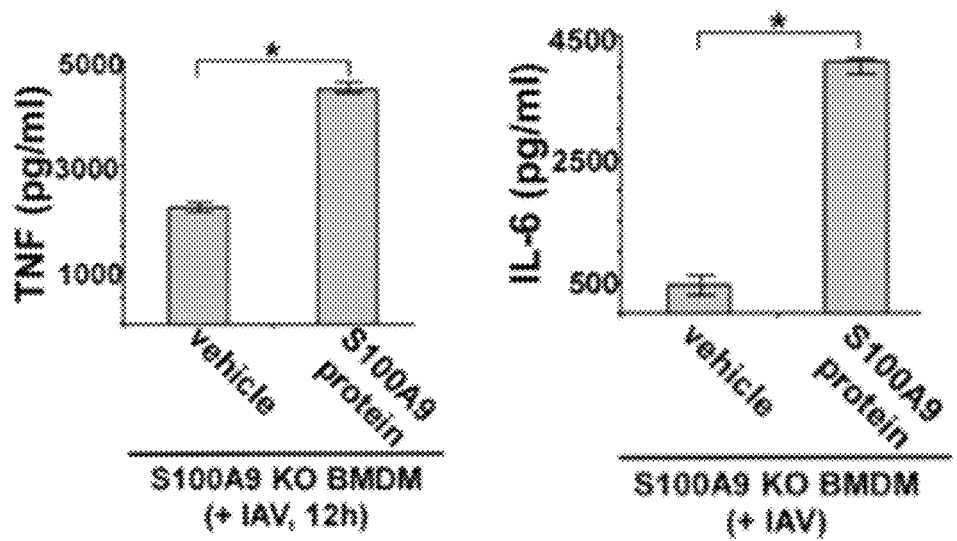

The finding that S100A9 contributes to the pro-inflammatory response during IAV infection was validated by using BMDMs derived from S100A9 KO mice. WT and S100A9 KO BMDMs were infected with IAV, after which TNF and IL-6 levels in the medium supernatant were measured by ELISA. As compared to WT cells, there were significant reductions in IL-6 (FIG. 4B) and TNF (FIG. 4C) production from infected S100A9 KO cells. Once again, this was a consequence of the loss of pro-inflammatory gene expression in IAV-infected S100A9 KO BMDMs. The critical function of secreted (extracellular-form) S100A9 during this response was apparent from the observation that addition of purified mouse S100A9 protein to S100A9 KO BMDMs restored the pro-inflammatory response in IAV-infected S100A9 KO BMDMs (FIG. 4D). This result also suggested that intracellular S100A9 does not play a role in inducing a pro-inflammatory response. Treatment of WT or S100A9 BMDMs with S100A9 protein did not alter IAV replication status in the corresponding cells (not shown). The inventors also observed production of S100A9 following treatment of BMDMs with synthetic dsRNA (poly-IC). The pro-inflammatory activity of S100A9 was specific for IAV and dsRNA (which serves as a replicative intermediate during IAV infection and induces DDX21/TRIF pathway) since dsRNA (poly-IC) dependent TNF and IL-6 release was significantly diminished in S100A9 KO cells, and treatment of KO cells with purified S100A9 protein restored the pro-inflammatory response in poly-IC treated S100A9 KO cells. In contrast, TNF and IL-6 release from S100A9 KO BMDMs was not affected following imiquimod (which activates TLR7 dependent pro-inflammatory response) treatment. In addition, treatment of WT and S100A9 KO BMDMs with TNF (to induce NF-κB dependent inflammatory response via TNF receptor) revealed similar levels of IL-6 production from both WT and KO cells.

During these studies it was observed that IAV replication (as deduced from IAV HA mRNA expression) was significantly reduced in S100A9 KO BMDMs compared to WT cells. This result suggested that although extracellular S100A9 plays a critical role in modulating pro-inflammatory response (FIG. 4D), intracellular S100A9 may be involved in negatively regulating antiviral factor expression/production or it is required for efficient virus infection/replication. This is not surprising in light of previous reports illustrating differential function of extracellular vs. intracellular S100 proteins.

The inventors observed S100A9 production from IAV-infected BMDMs at 4 hours postinfection (FIG. 1C) and that TNF and IL-6 are produced from IAV-infected BMDMs at 8-12 hours postinfection (not shown); these cytokines are undetectable at 4 hours postinfection (not shown). Thus, S100A9 secretion and production of early pro-inflammatory mediators (e.g. TNF, IL-6) are temporally regulated during IAV-infection. Therefore, extracellular S100A9 is a key regulator of the pro-inflammatory response during IAV infection.

Extracellular S100A9 promotes apoptosis during IAV infection. Macrophages undergo apoptosis during IAV infection (Hoeve et al. (2012) PLoS One 7: e29443; Huang et al. (2011) Am J Respir Crit Care Med 184: 259-268). Several studies have demonstrated that S100A9 has a pro-apoptotic function in epithelial cells, muscle cells, and neutrophils (Atallah et al. (2012) PLoS One 7: e29333; Ghavami et al. (2010) Cell Res 20: 314-331; Li et al. (2009) Biochem J 422: 363-372; Viemann et al. (2007) Blood 109: 2453-2460; Seeliger et al. (2003) Am j pathol 163: 947-956), but no apoptosis-inducing activity of S100A9 (or any other S100 proteins) in macrophages has been reported. Since IAV infection resulted in high levels of S100A9 secretion, the inventors examined the ability of extracellular S100A9 to induce apoptosis in macrophages and the role of secreted S100A9 in apoptotic induction during IAV infection.

Figure 5A:
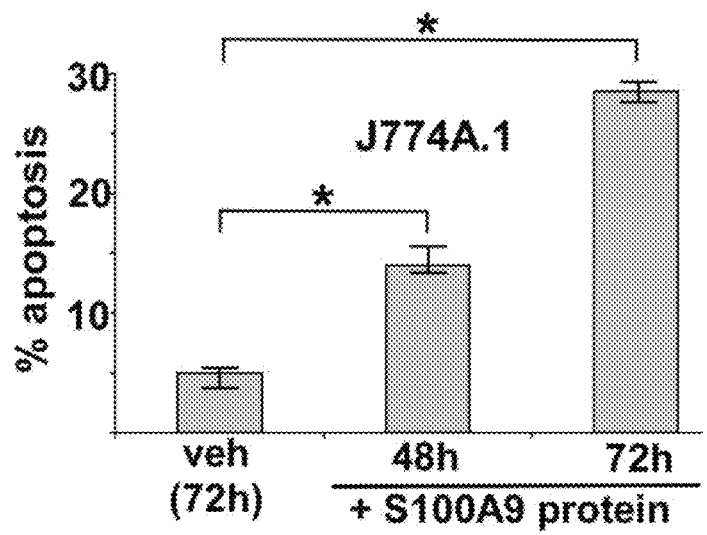
FIGS. 5A-5C. Extracellular S100A9 protein triggers apoptosis in macrophages and S100A9 regulates apoptosis during IAV infection.
Figure 5B:
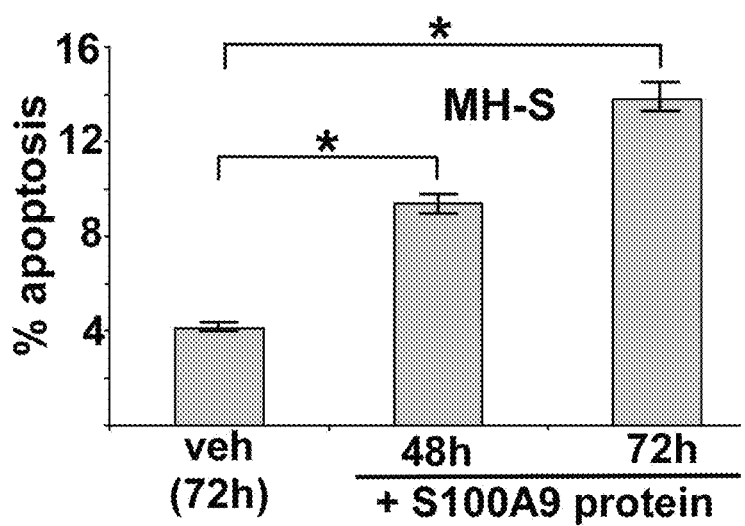

J774A.1 and MH-S macrophages were treated with purified S100A9 protein for 48 and 72 h, then examined the apoptotic status of cells by monitoring annexin V and PI staining. The apoptosis rate was calculated based on the number of annexin V positive/PI negative cells (denoting early apoptosis)+number of annexin V positive/PI-positive cells (denoting late apoptosis) per total number of cells. It was noted that apoptosis in S100A9 protein-treated mouse macrophages (FIGS. 5A and 5B). The result obtained with annexin V and PI staining was confirmed by performing TUNEL analysis. Similar results were obtained following treatment of human U937 macrophages (not shown).

Figure 5C:
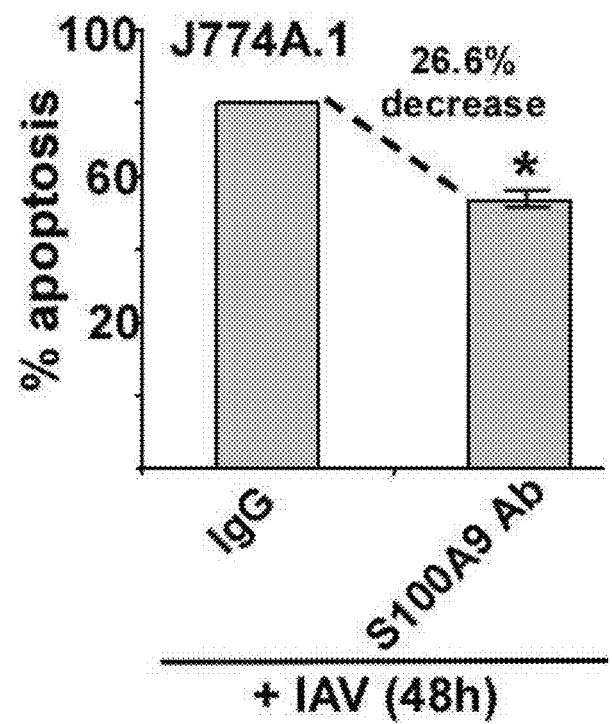

Since IAV infection triggers S100A9 secretion, the inventors next examined whether extracellular S100A9 has a role in apoptosis of IAV-infected macrophages. J774A.1 macrophages were infected with IAV for 48 hours in the presence of either control antibody (control IgG) or S100A9 blocking antibody. Significantly diminished apoptosis (reduction of 27%) occurred in macrophages treated with S100A9 antibody (FIG. 5C). These results were further confirmed by TUNEL analysis. Thus, extracellular S100A9 has a critical function in regulating apoptosis of IAV-infected macrophages.

Figure 6A:
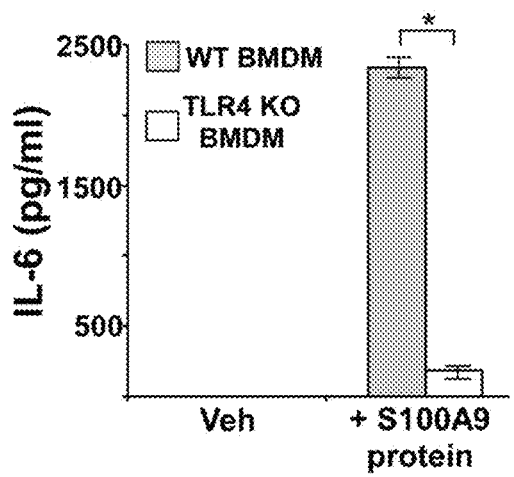
FIGS. 6A-6E. S100A9 activates TLR4/MyD88 pathway and activation of TLR4/MyD88 pathway is essential for IAV-induced pro-inflammatory response. Primary bone marrow derived macrophages (BMDM) isolated from wild-type (WT) and TLR4 knockout (KO) mice were incubated with purified recombinant mouse S100A9 protein (5 ug/mL). The medium supernatant was collected to assess levels of mouse IL-6 (FIG. 6A) and mouse TNF-α (TNF) (FIG. 6B) by ELISA.
Figure 6B:
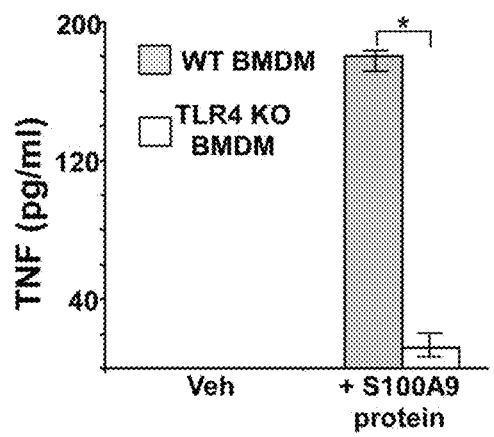

The TLR4/MyD88 pathway is required for S100A9-mediated pro-inflammatory response following IAV infection. Previous studies have found that optimal TLR4 activation by LPS in bone-marrow cells required the activity of extracellular S100A9/S100A8 complex (Vogl et al. (2007) Nat Med 13: 1042-1049). However, it is not known whether S100A9 alone activates TLR4, especially in macrophages. In addition, there has been no report of DAMP proteins like S100A9 activating PRR signaling during virus infection. Therefore, the inventors investigated the role of the TLR4/MyD88 pathway in the macrophage pro-inflammatory response by S100A9 alone (in the absence of S100A8), and the function of the S100A9/TLR4/MyD88 pathway in regulating the pro-inflammatory response in IAV-infected macrophages. WT and TLR4 KO BMDMs were incubated with purified S100A9 protein, and then measured IL-6 (FIG. 6A) and TNF (FIG. 6B) levels by ELISA. Drastic loss of IL-6 and TNF production was detected in S100A9 protein-treated TLR4 KO BMDMs (FIGS. 6A and 6B), indicating that TLR4 is absolutely required for the S100A9-mediated response. Drastic reductions in IL-6 and TNF transcripts occurred in S100A9 protein treated TLR4 KO cells.

Figure 6C:
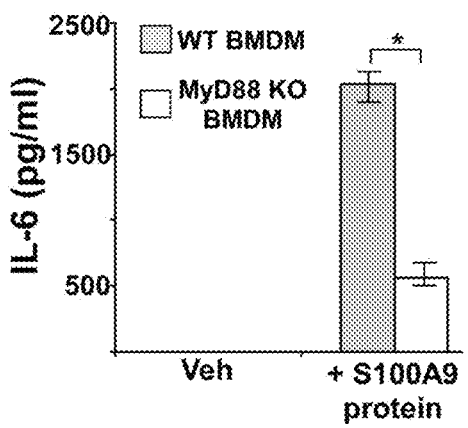

Since MyD88 is one of the critical adaptors for activated TLR4, the role of MyD88 was investigated by using MyD88 KO BMDMs. Incubation of WT and MyD88 KO BMDMs with purified S100A9 protein significantly reduced production of IL-6 (FIG. 6C) and TNF (not shown) from MyD88 KO cells. The loss of cytokine protein production was due to reduced TNF and IL-6 gene expression in MyD88 KO BMDMs, thus, demonstrating that the TLR4/MyD88 pathway is required for the S100A9-mediated pro-inflammatory response.

Figure 6D:
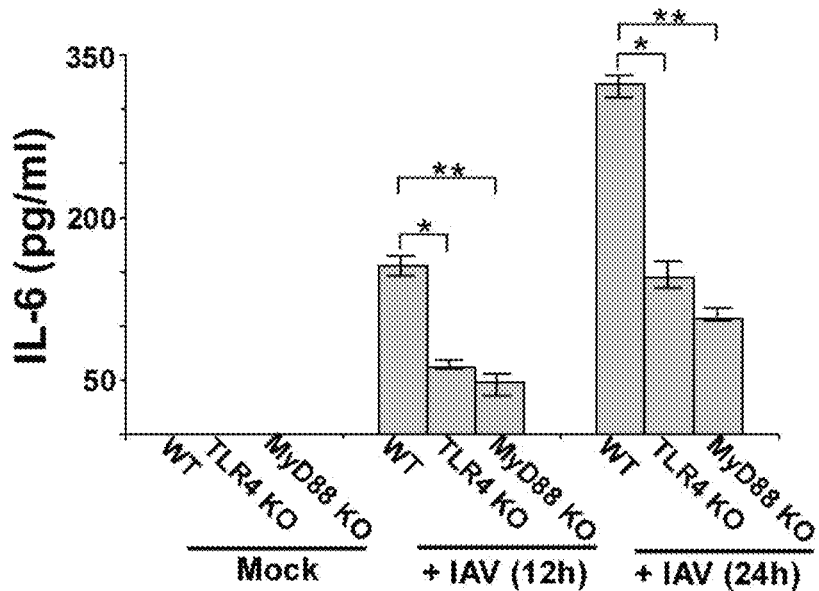
Figure 6E:
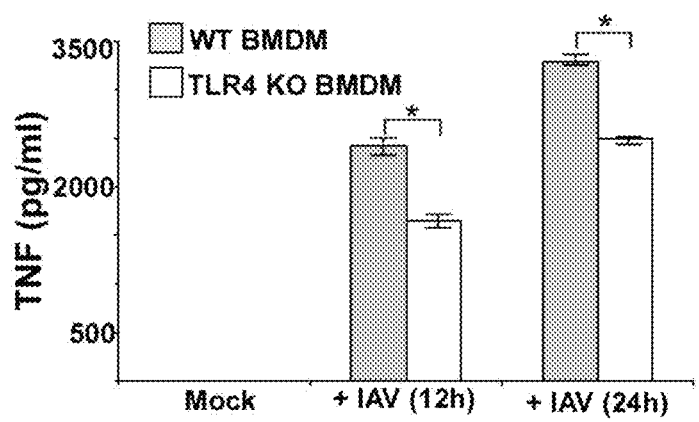

The role of TLR4/MyD88 in stimulating the pro-inflammatory response following IAV infection was studied. After WT, MyD88 KO, and TLR4 KO BMDMs were infected with IAV, IL-6 levels were assessed by ELISA. The study revealed that TLR4/MyD88 is an essential regulator of pro-inflammatory response during IAV infection, since significant reduction in IL-6 (FIG. 6D) and TNF (FIG. 6E) production was noted in IAV infected TLR4 KO (FIGS. 6D and 6E) and MyD88 KO (FIG. 6D) BMDMs. RT-PCR analysis demonstrated diminished expression of IL-6 mRNA in TLR4 KO and MyD88 KO BMDMs. Similarly, it was noted that significant reduction in TNF production from IAV-infected TLR4 KO (FIG. 6E) and MyD88 KO (not shown) BMDMs. The observed effect was independent of virus replication since compared to WT cells, no change in HA mRNA expression was noted in TLR4 KO and MyD88 KO cells. Thus, TLR4/MyD88 activation is a key step for inducing the S100A9-mediated pro-inflammatory response. Also, the S100A9/TLR4/MyD88 pathway is a crucial regulator of the pro-inflammatory response during IAV infection.

Figure 7A:
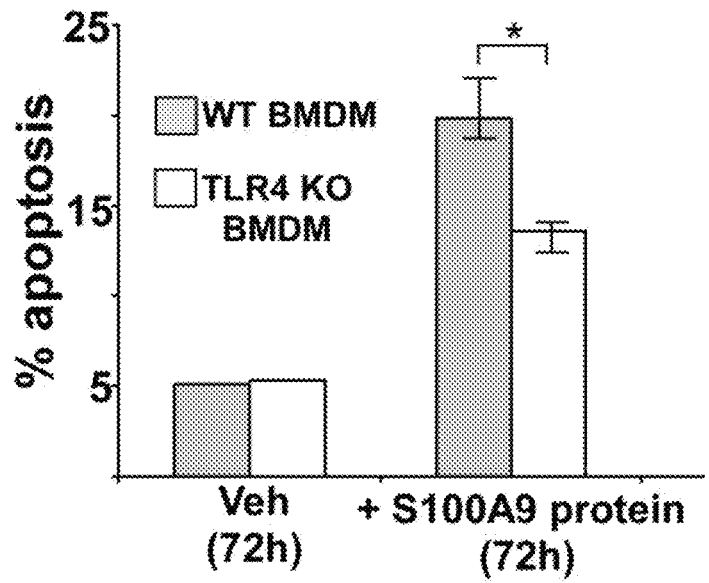
FIGS. 7A-7D. Activated TLR4/MyD88 pathway promotes S100A9-mediated apoptosis and is required for optimal apoptosis of IAV infected cells.

TLR4/MyD88 pathway is required for apoptosis during IAV infection. The study showed that extracellular S100A9 uses TLR4/MyD88 signaling for the pro-inflammatory response during IAV infection. TLR4 activation has been associated with apoptosis induction via various mechanisms, including activation of the pro-apoptotic function of NF-κB, modulation of tumor-suppresser expression or function etc. (Yi et al. (2012) PLoS One 7: e36560; Equils et al. (2006) J Immunol 177: 1257-1263; De Trez et al. (2005) J Immunol 175: 839-846; Basak et al. (2005) J Immunol 174: 5672-5680; Neal et al. (2012) J Biol Chem 287: 37296-37308; Sanchez et al. (2010) Cell Immunol 260: 128-136; Suzuki et al. (2004) Infect Immun 72: 1856-1865). To assess the role of TLR4 in S100A9-mediated apoptosis, WT and TLR4 KO BMDMs were treated with purified S100A9 protein for 72 hours. Treatment of WT BMDMs with S100A9 protein induced apoptosis (FIG. 7A), which was consistent with previous findings. However, significant loss of apoptosis was observed in S100A9 protein-treated TLR4 KO BMDMs (FIG. 7A).

Figure 7B:
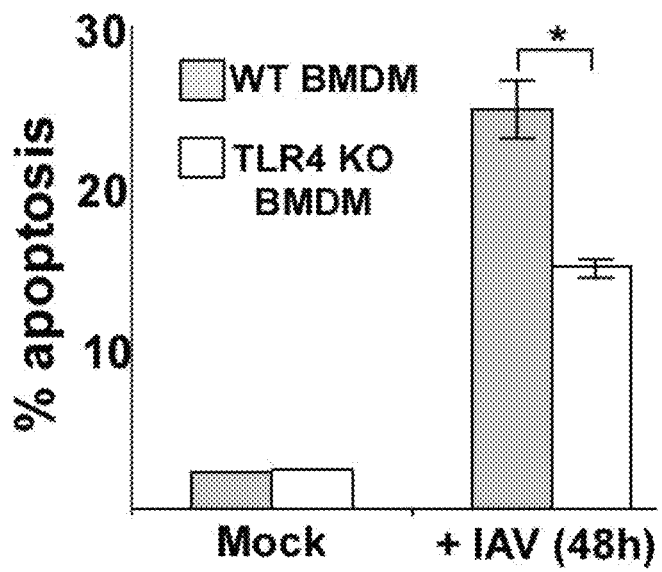
Figure 7C:
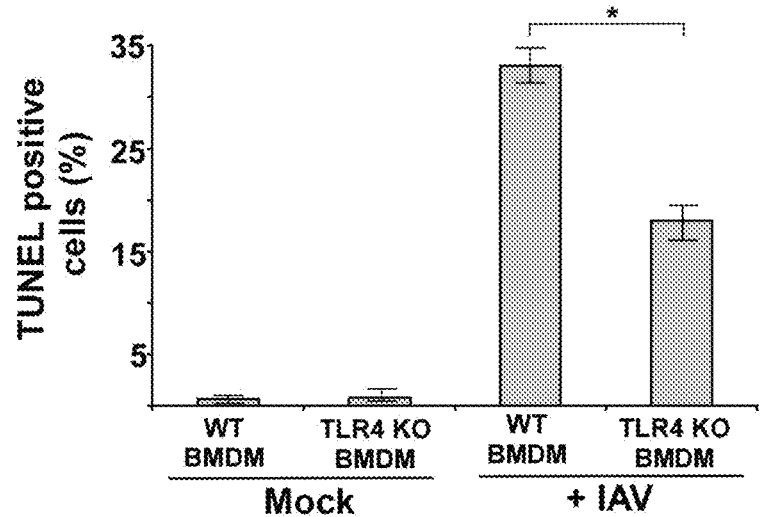
Figure 7D:
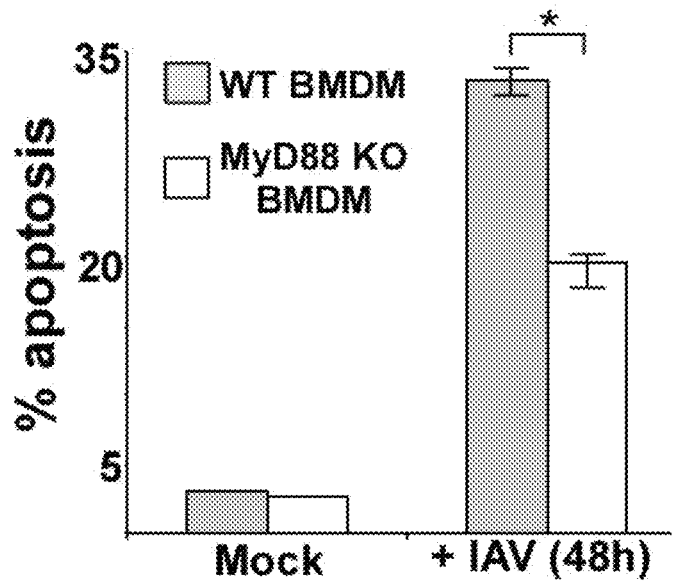

The role of TLR4 and MyD88 was examined in apoptosis induction during IAV infection. WT and TLR4 KO BMDMs were infected with IAV and evaluated apoptosis 48 hours later. Apoptosis analysis by annexin V staining (FIG. 7B) and TUNEL (FIG. 7C) revealed that while IAV infection resulted in apoptosis of WT macrophages, a significant reduction in apoptosis was detected in TLR4 KO cells. Diminished apoptosis was also observed in infected MyD88 KO BMDMs (FIG. 7D), indicating that MyD88 is also required during this event. Thus, the S100A9/TLR4/MyD88 pathway constitutes one of the mechanisms that modulate apoptosis of IAV-infected cells.

Figure 8A:
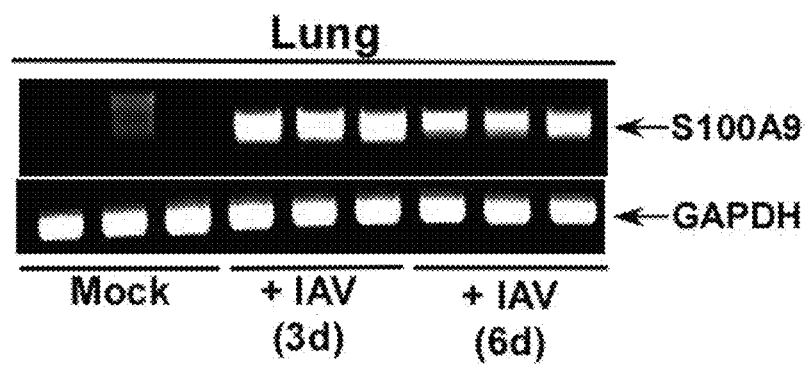
FIGS. 8A-8D. S100A9 expression and production in the IAV infected respiratory tract.
Figure 8B:
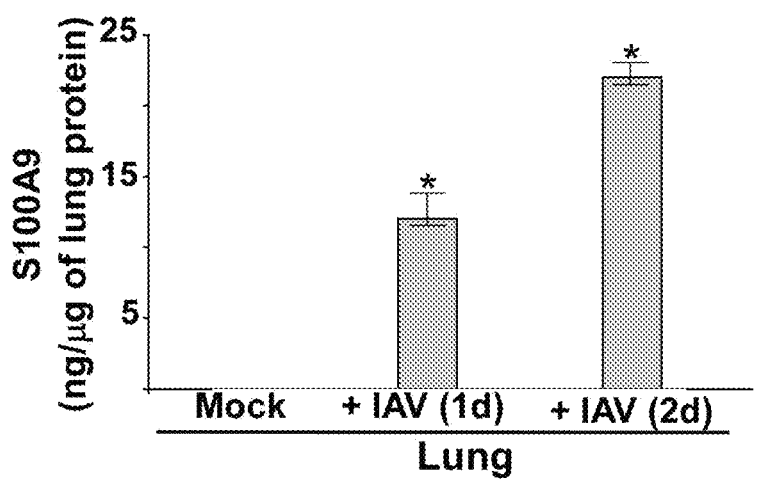
Figure 8C:
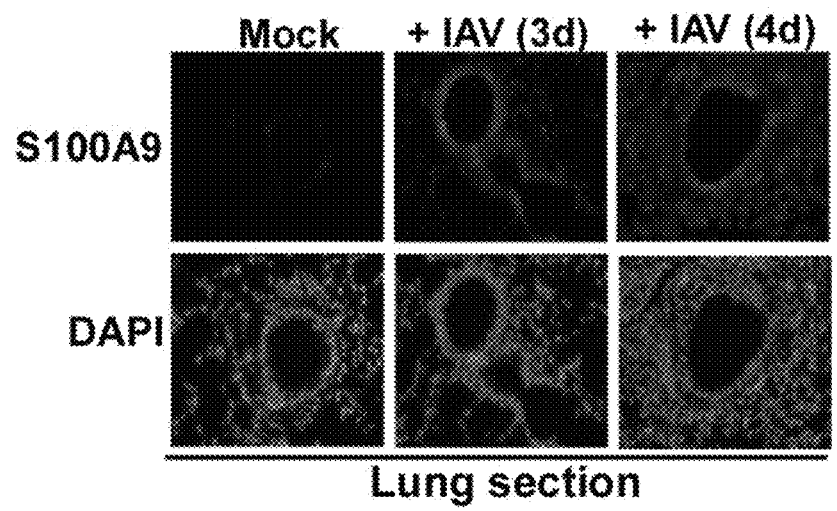
Figure 8D:
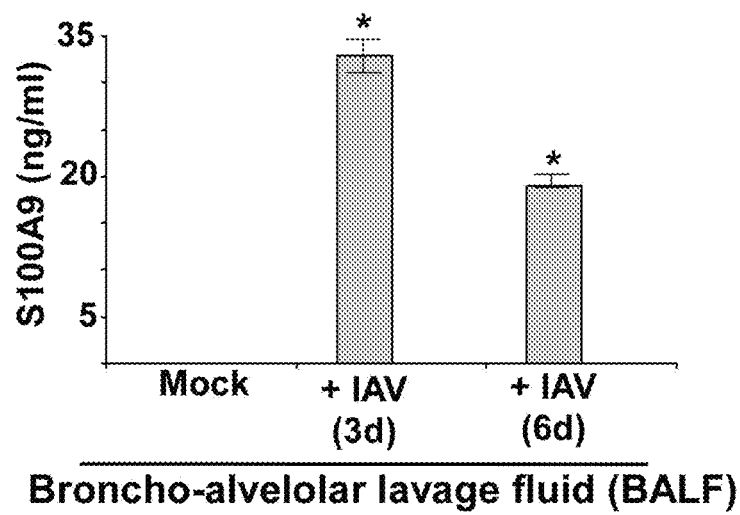

S100A9 expression in IAV-infected mouse respiratory tract. To establish the in vivo role of S100A9 in regulating innate response during IAV infection of the airway, S100A9 expression was evaluated and its secretion in the IAV-infected mouse respiratory tract. Mice were intratracheally inoculated with IAV and, at 1-6 days postinfection, lungs were harvested. S100A9 mRNA expression in the lungs were analyzed by RT-PCR. S100A9 transcripts were observed in infected lungs but not in lungs from uninfected animals (FIG. 8A), indicating that IAV infection led to robust induction of S100A9 gene expression. High levels of S100A9 protein were detected in the lungs of IAV-infected mice (FIG. 8B). Immunohistochemical analysis of lung sections confirmed the presence of S100A9 protein in IAV-infected animals (FIG. 8C), while S100A9 was nearly undetectable in mock-infected lungs. Analysis of bronchoalveolar lavage fluid (BALF) by ELISA confirmed the presence of S100A9 protein in the airway of IAV-infected animals (FIG. 8D). Thus, IAV infection of the respiratory tract results in induction of S100A9 gene expression and secretion of S100A9 protein in the airway.

Extracellular S100A9 regulates IAV susceptibility and lung inflammation. Macrophages play a vital role in the innate response to IAV infection by producing pro-inflammatory mediators that determine the inflammation status in the lung (Peschke et al. (1993) Immunobiology 189: 340-355; Herold et al. (2008) J Exp Med 205: 3065-3077; Hoeve et al. (2012) PLoS One 7: e29443; Huang et al. (2011) Am J Respir Crit Care Med 184: 259-268). Moreover, debris from dead cells, originating from apoptosis of immune cells, contributes to airway inflammation (Herold et al. (2008) J Exp Med 205: 3065-3077; Hoeve et al. (2012) PLoS One 7: e29443; Huang et al. (2011) Am J Respir Crit Care Med 184: 259-268; Welliver et al. (2007) J Infect Dis 195: 1126-1136; Hinshaw et al. (1994) J Virol 68: 3667-3673; Zhang et al. (2010) Virol J 7: 51; Lu et al. (2010) J Gen Virol 91: 1439-1449; Brydon et al. (2005) FEMS Microbiol Rev 29: 837-850; Vandivier et al. (2006) CHEST 129: 1673-1682). Since extracellular S100A9 acted as a positive regulator of pro-inflammatory response and induced apoptosis, it was hypothesized that extracellular S100A9 exacerbates IAV-associated lung disease. To test this, the inventors used anti-S100A9 blocking antibody, which neutralizes extracellular (secreted) S100A9 protein.

Anti-S100A9 antibody was used instead of doing in vivo studies with S100A9 KO mice because S100 proteins have both intracellular functions (such as cytoskeletal rearrangement, cell metabolism, intracellular calcium response etc.) and extracellular functions (Hermann et al. (2012) Front Pharmacol 3: 67; Halayko and Ghavami (2009) Can J Physiol Pharmacol 87: 743-755). Since the inventors have elucidated a role of extracellular (secreted form) S100A9, results from KO mice might not distinguish whether the observed effects are due to activity of extracellular S100A9 or intracellular S100A9 function. Most importantly the studies demonstrated that intracellular S100A9 could be involved in negatively regulating antiviral response or it is required for IAV infection/replication, since reduced virus replication was noted in S100A9 KO BMDM compared to WT cells. In that scenario, S100A9 KO mice may not serve as an appropriate model to study IAV-induced pro-inflammatory (and apoptotic) response in vivo, since viral burden in the lung is directly proportional to the degree of pro-inflammatory (and apoptotic) response (i.e. if there is less viral burden then concomitantly reduced pro-inflammatory response and apoptosis will occur). However, neutralizing the activity of extracellular S100A9 with S100A9 blocking antibody did not alter IAV replication in vitro and in vivo. The inventors therefore used anti-S100A9 blocking antibody to specifically inhibit the activity of extracellular S100A9 in mice. The inventors have previously shown that anti-S100A9 blocking antibody has extracellular S100A9 blocking activity (Ryckman et al. (2003) J Immunol 170: 3233-3242; Anceriz et al. (2007) Biochem Biophys Res Commun 354: 84-89; Cesaro et al. (2012) PLoS One 7: e45478; Simard et al. (2010) J Leukoc Biol 87: 905-914; Simard et al. (2011) J Immunol 186: 3622-3631; Raquil et al. (2008) J Immunol 180: 3366-3374; Vandal et al. (2003) J Immunol 171: 2602-2609. Specifically, intraperitoneal (i.p) injection of S100A9 blocking antibody inhibited the activity of mouse S100A9 during S. pneumoniae infection (Raquil et al. (2008) J Immunol 180: 3366-3374). Thus, this antibody is useful to assess the functional role of extracellular (secreted form) S100A9. Furthermore, similar levels of S100A9 protein were detected in the BALF of control IgG-treated and S100A9-antibody treated mice. Thus, i.p.-injected anti-S100A9 antibody did not significantly affect S100A9 protein production in the airway-lumen following IAV infection. As in previous reports, the inventors detected anti-S100A9 antibody (administered i.p.) in lung homogenate. Thus, anti-S100A9 antibody could effectively block lung-localized S100A9 during IAV infection (Raquil et al. (2008) J Immunol 180: 3366-3374; Kim et al. (2012) Am J Respir Cell Mol Biol 47: 372-378; Toews et al. (1985) Infect Immun 48: 343-349). The clinical significance of utilizing neutralizing antibody is obvious from possible passive immunization with S100A9 antibody as a new therapeutic strategy to control lung inflammation and associated lung disease during IAV infection.

Initially, the inventors investigated the role of secreted S100A9 in regulating IAV susceptibility. For these studies, mice were i.p. injected with either control IgG or anti-S100A9 blocking antibody. One day later, mice were infected with IAV via intra-tracheal (I.T) inoculation. Survival of IAV-infected mice was monitored until 8 days postinfection. Blocking S100A9 activity significantly reduced the mortality of IAV-infected mice (FIG. 9A), demonstrating that extracellular S100A9 is a key regulator of IAV susceptibility. Extracellular S100A9 also contributes to morbidity since mice treated with S100A9 blocking antibody exhibited reduced weight loss upon IAV infection. Thus, extracellular S100A9 contributes to both IAV-induced mortality and morbidity.

Figure 9A:
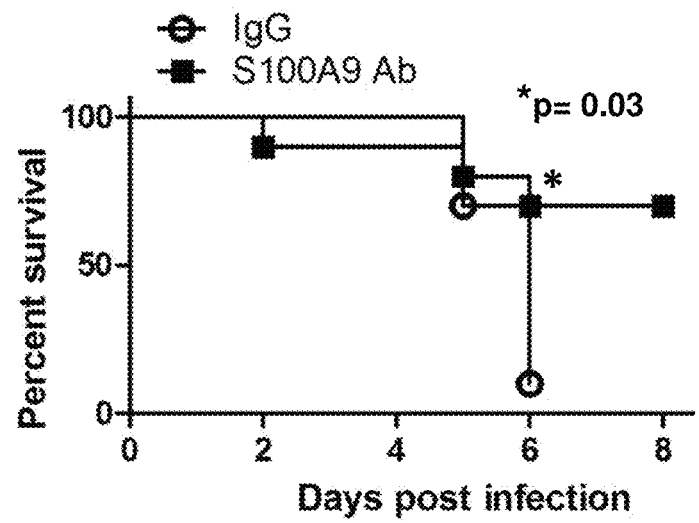
FIGS. 9A-9E. S100A9 contributes to enhanced susceptibility and inflammation during IAV infection and S100A9 regulates pro-inflammatory response in the respiratory tract of IAV infected mice.
Figure 9B:
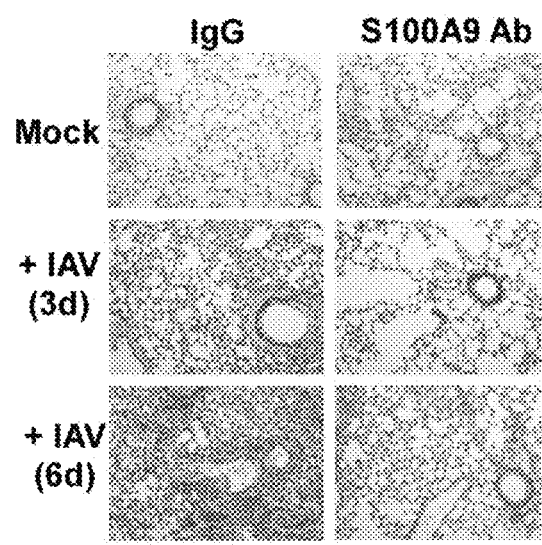

In addition, inflammation was reduced following inhibition of extracellular S100A9 activity (FIG. 9B). These results demonstrated that extracellular S100A9 contributes to the severity of IAV-associated lung inflammation and serves as a critical host factor for heightened IAV susceptibility and IAV-induced death. The clinical significance of our result is borne out by the possibility of passive immunization with anti-S100A9 antibody to reduce the severity of respiratory disease associated with IAV infection.

Figure 9C:
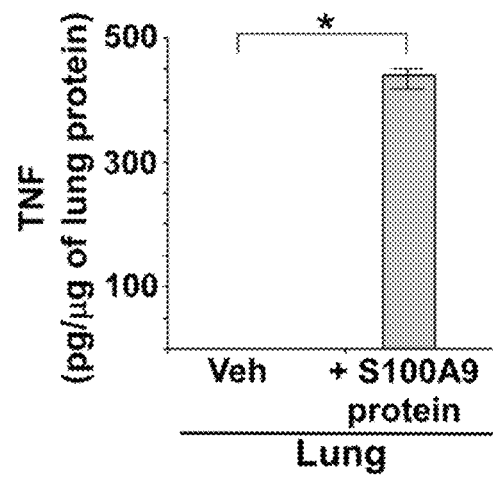

Extracellular S100A9 controls the pro-inflammatory response in IAV-infected lungs. The inventors have identified extracellular (secreted) S100A9 as a critical regulator of the pro-inflammatory response following IAV infection of macrophages. To examine the physiological role of secreted S100A9 in lung inflammation, the inventors tested whether intratracheal (I.T.) administration of purified S100A9 protein would trigger a pro-inflammatory response in the lungs. Indeed, this led to production of TNF (FIG. 9C) and IL-6 in the respiratory tract due to S100A9-mediated upregulation of TNF and IL-6 gene expression in the lung (not shown). The ability of S100A9 protein to trigger pro-inflammatory mediators in the lung is further reflected by observing airway inflammation in S100A9 protein administered (via I.T) mice.

Figure 9D:
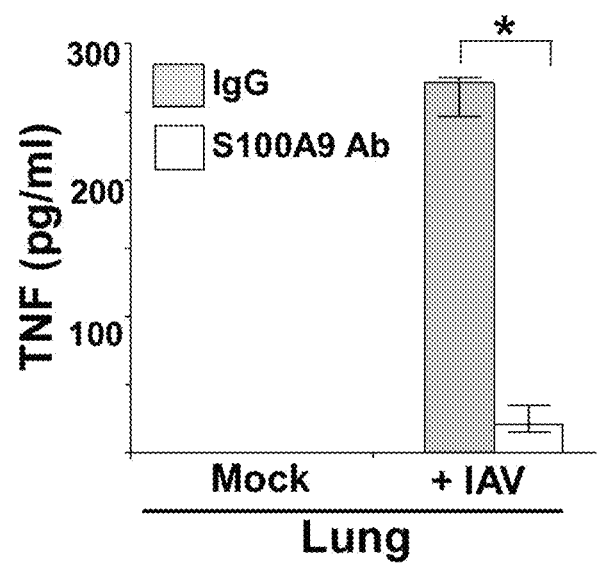

Based on this observation, the role of extracellular S100A9 in airway pro-inflammatory response following IAV infection was examined. Mice were given i.p. injections of control IgG antibody or anti-S100A9 blocking antibody. At 1 d post-antibody treatment, mice were infected with IAV via I.T route. Levels of IL-6 and TNF in the lung were measured by ELISA. Extracellular S100A9 contributes to production of pro-inflammatory mediators during infection as evident from reduced TNF (FIG. 9D) and IL-6 levels in the lung of S100A9 antibody treated mice. Reduced pro-inflammatory cytokine production was caused by loss of TNF and IL-6 mRNAs in the lungs of IAV-infected mice treated with S100A9 blocking antibody. Diminished proinflammatory response is not due to reduced IAV infection, since both control antibody and S100A9 antibody treated mice exhibited similar IAV infection status (i.e. viral burden). Interestingly, S100A9 antibody could also be utilized as therapeutics to control IAV-associated disease, since administration of S100A9 blocking antibody after IAV infection significantly reduced pro-inflammatory response and lung inflammation.

In order to provide evidence for direct neutralization of S100A9 activity in the airway following i.p. administration of S100A9 antibody, S100A9 antibody was administered (via i.p.) to mice and after one day (to exactly mimic IAV infection studies) mice were inoculated with S100A9 protein via I.T route. Significant inhibition in pro-inflammatory activity was noted in the presence of S100A9 antibody, which shows that i.p. administered blocking antibody can neutralize S100A9 protein in the airway.

Figure 9E:
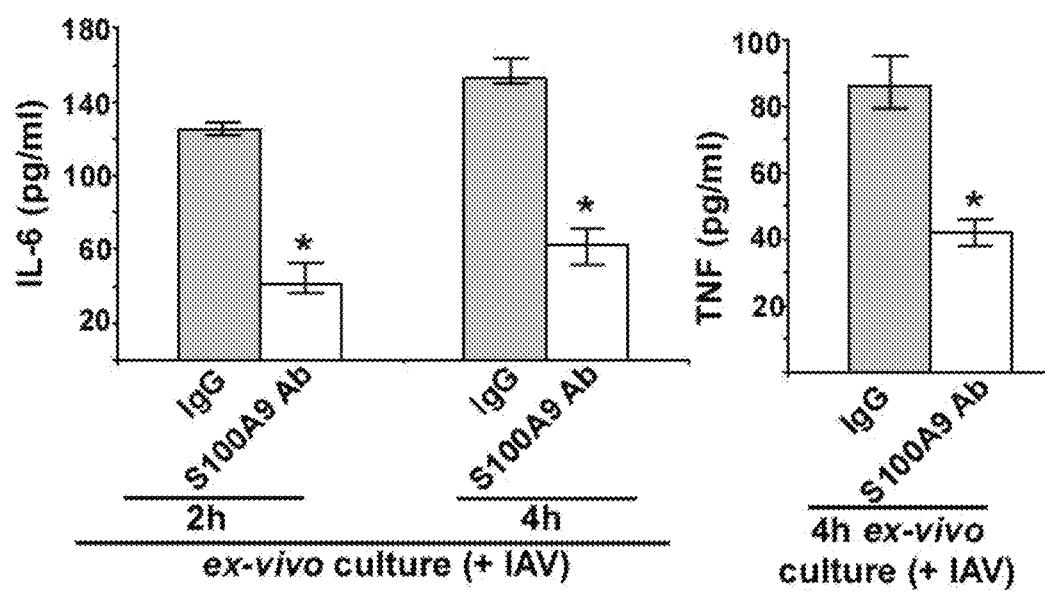

The role of extracellular S100A9 was further validated by conducting ex vivo experiment with BALF-associated cells derived from IAV infected mice administered (via i.p) with either control antibody or S100A9 blocking antibody. Significant reduction in IL-6 and TNF production from BALF cells was observed in S100A9 blocking antibody treated mice (FIG. 9E). This result once again validates blocking of S100A9 activity in the alveolar space localized (i.e. present in the BALF) cells. These studies illustrate the importance of secreted S100A9 in regulating pro-inflammatory cytokine gene expression and production during IAV infection of the airway.

Figure 10A:
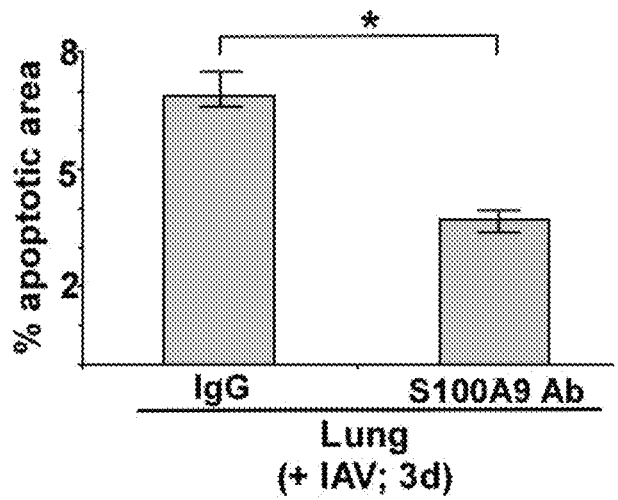
FIGS. 10A-10C. Extracellular S100A9 promotes optimal apoptosis in the lung of IAV infected mice.
Figure 10B:
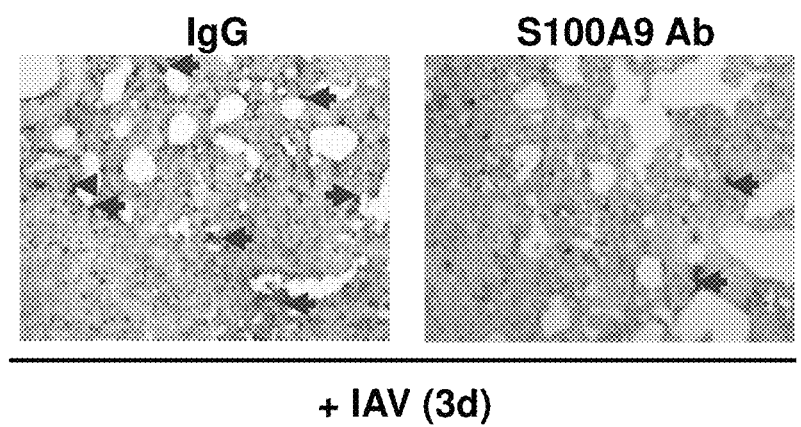
Figure 10C:
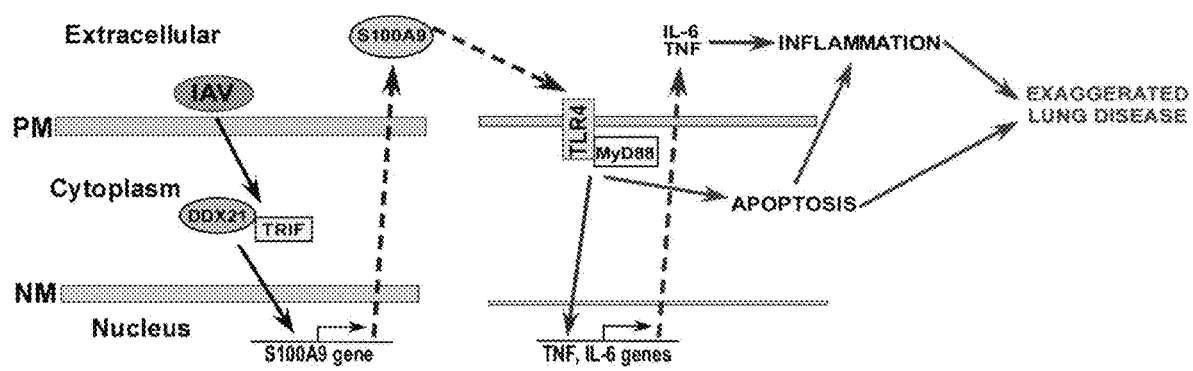

Extracellular S100A9 promotes apoptosis in the respiratory tract of IAV-infected mice. The studies with macrophages have illuminated a vital role of extracellular S100A9 in inducing apoptosis of IAV-infected cells. The inventors have extended those observations in mice to establish the in vivo physiological relevance of extracellular S100A9 as a regulator of apoptosis. Further, it is known that apoptosis significantly contributes to IAV infection severity and associated lung disease. Therefore, reduced apoptosis in IAV-infected S100A9-blocked mice may contribute to reduced susceptibility and diminished airway disease (as shown in FIGS. 9A and 9B). To examine this possibility, mice treated with control IgG and S100A9 blocking antibody were inoculated with IAV via the I.T route. On the third day post-infection, in situ TUNEL assay with lung sections were performed to determine the apoptotic status of the IAV-infected respiratory tract. The inventors found significantly less apoptosis in the lungs of mice given S100A9 blocking antibody than in the lungs of control mice (FIGS. 10A and 10B). These results demonstrated that secreted S100A9 is a pivotal regulator of lung apoptosis following IAV infection.

Methods

Virus, cell culture, mice. Influenza A [A/PR/8/34 (H1N1)] virus was grown in the allantoic cavities of 10-day-old embryonated eggs (Sabbah et al. (2009) Nat Immunol 10: 1073-1080; Mgbemena et al. (2012) J Immunol 189: 606-615). Virus was purified by centrifuging two times on discontinuous sucrose gradients (Sabbah et al. (2009) Nat Immunol 10: 1073-1080; Mgbemena et al. (2012) J Immunol 189: 606-615; Ueba (1978) Acta Med Okayama 32: 265-272). J774A.1 cells were maintained in DMEM supplemented with 10% fetal bovine serum (FBS), penicillin, streptomycin, and glutamine. U937 cells were maintained in RPMI 1640 medium supplemented with 10% FBS, 100 IU/mL penicillin, 100m/mL streptomycin, 1 mM sodium pyruvate, and 100 nM HEPES. MH-S cells were maintained in RPMI 1640 medium supplemented with 10% FBS, 100 IU/mL penicillin, and 100m/mL streptomycin. Bone-marrow-derived macrophages (BMDMs) were obtained from femurs and tibias of wild-type (WT) and knock-out mice and were cultured for 6-8 days as described earlier (Sabbah et al. (2009) Nat Immunol 10: 1073-1080; Mgbemena et al. (2012) J Immunol 189: 606-615). Cells were plated on 12-well plates containing RPMI, 10% FBS, 100 IU/mL penicillin, 100m/mL streptomycin, and 20 ng/ml GM-CSF. Alveolar macrophages were obtained from the bronchoalveolar lavage fluid (BALF) of wild-type C57BL/6 mice. The IAV titer was monitored by plaque assay analysis with MDCK cells.

S100A9 KO mice were generated at University of Laval, Quebec, Canada. Other KO mice (TLR4, TLR2, TRAM, TRIF, TIRAP) were originally provided by Dr. Doug Golenbock (University of Massachusetts Medical School, Worcester, MA). TLR3 KO, TLR7 KO and MyD88 KO mice were obtained from Jackson Laboratory, Bar Harbor, ME Antibodies and proteins. Murine S100A9 neutralizing antibody purified IgG from the serum of S100A9 immunized rabbits was generated as described previously (Ryckman et al. (2003) J Immunol 170: 3233-3242; Anceriz et al. (2007) Biochem Biophys Res Commun 354: 84-89). This antibody has been successfully used to block the activity of extracellular mouse S100A9 (Ryckman et al. (2003) J Immunol 170: 3233-3242; Anceriz et al. (2007) Biochem Biophys Res Commun 354: 84-89; Cesaro et al. (2012) PLoS One 7: e45478; Simard et al. (2010) J Leukoc Biol 87: 905-914; Simard et al. (2011) J Immunol 186: 3622-3631; Raquil et al. (2008) J Immunol 180: 3366-3374; Vandal et al. (2003) J Immunol 171: 2602-2609). Human S100A9 antibody was acquired from AbCam, Cambridge, MA (goat anti-human S100A9 antibody) and R&D Systems (mouse anti-human antibody). Recombinant human and mouse S100A9 proteins were generated as previously described (Ryckman et al. (2003) J Immunol 170: 3233-3242; Anceriz et al. (2007) Biochem Biophys Res Commun 354: 84-89; Cesaro et al. (2012) PLoS One 7: e45478; Simard et al. (2010) J Leukoc Biol 87: 905-914; Simard et al. (2011) J Immunol 186: 3622-3631; Raquil et al. (2008) J Immunol 180: 3366-3374; Vandal et al. (2003) J Immunol 171: 2602-2609). Briefly, full length human S100A9 cDNA was cloned into pET28 expression vector (Novagen, Madison, WI). S100A9 protein expression was induced with 1 mM isopropyl β-D-thiogalactoside (IPTG) in E. coli HMS174 (Boehringer Mannheim, Mannheim, Germany) for 16 h at 16° C. After IPTG treatment, the bacteria were centrifuged at 5000×g for 10 min and the pellet was re-suspended in PBS [(containing NaCl (0.5 M) and imidazole (1 mM)] and lysed by sonication. Upon centrifuging the lysate at 55,000×g for 30 min at 4° C., the supernatant was collected. Recombinant His-Tag S100A9 was purified by using a nickel column. S100A9 bound to the column was incubated with 10 U of biotinylated thrombin (Novagen) (for 20 h at room temperature) to free S100A9 from its His-Tag. Recombinant S100A9 was then eluted with PBS. The digestion and elution processes were repeated one more time to cleave the remaining undigested recombinant proteins, and streptavidin-agarose (Novagen) was added to remove contaminating thrombin. Finally, the protein preparation was passed through a polymyxin B-agarose column (Pierce, Rockford, IL) to remove endotoxins.

Recombinant proteins were prepared in Hank's buffered salt solution (HBSS) buffer. The absence of endotoxin contamination in antibody and protein preparations was confirmed using the limulus amebocyte assay (Cambrex).

Reverse transcription-PCR (RT-PCR). Total RNA was extracted using Tri Reagent (Invitrogen). cDNA was synthesized using a High-Capacity cDNA Reverse Transcription Kit (Applied Biosystems). PCR was done using 0.25 units of Taq polymerase, 10 pmol of each oligonucleotide primer, 1 mM $MgCl_2$, and 100 μM deoxynucleotide triphosphates in a final reaction volume of 25 μl. Following amplification, the PCR products were analyzed on 1.5% agarose gel. Equal loading in each well was confirmed by analyzing expression of the housekeeping gene glyceraldehyde-3-phosphate dehydrogenase (GAPDH). The primers used to detect the indicated genes by RT-PCR were:

```
GAPDH forward,
                                    (SEQ ID NO: 1)
5'-GTCAGTGGTGGACCTGACCT, GAPDH reverse,
                                    (SEQ ID NO: 2)
5'-AGGGGTCTACATGGCAACTG, Mouse GAPDH forward,
                                    (SEQ ID NO: 3)
5'-GCCAAGGTCATCCATGACAACTTTGG, Mouse GAPDH reverse,
                                    (SEQ ID NO: 4)
5'-GCCTGCTTCACCACCTTCTTGATGTC Mouse S100A9 forward,
                                    (SEQ ID NO:5)
5'-GTCCTGGTTTGTGTCCAGGT, Mouse S100A9 reverse,
                                    (SEQ ID NO:6)
5'-TCATCGACACCTTCCATCAA Mouse DDX21 forward,
                                    (SEQ ID NO: 7)
5'-GATCCCCCTAAATCCAGGAA, Mouse DDX21 reverse,
                                    (SEQ ID NO: 8)
5'-TTCGGAAGGCTCCTCTGTTA Mouse TNF-α forward,
                                    (SEQ ID NO: 9)
5'-CCTGTAGCCCACGTCGTAGC, Mouse TNF-α reverse,
                                    (SEQ ID NO: 10)
5'-TTGACCTCAGCGCTGAGTTG Mouse IL-6 forward,
                                    (SEQ ID NO: 11)
5'-TTGCCTTCTTGGGACTGATGCT, Mouse IL-6 reverse,
                                    (SEQ ID NO: 12)
5'-GTATCTCTCTGAAGGACTCTGG IAV HA forward,
                                    (SEQ ID NO: 13)
5'-CCCAAGGAAAGTTCATGG, IAV HA reverse,
                                    (SEQ ID NO: 14)
5'-GAACACCCCATAGTACAAGG
```

Viral infection of cells. U937 cells, alvelolar macrophages, BMDM, MH-S, and J774A.1 were infected with purified IAV [1 multiplicity of infection (MOI)-2 MOI as indicated] in serum-free, antibiotic-free OPTI-MEM medium (Gibco). Virus adsorption was done for 1.5 h at 37° C., after which cells were washed twice with PBS. Infection was continued in the presence of serum containing DMEM or RPMI medium for the specified time points.

In some experiments, cells were infected in the presence of 2 ng-10 ng/ml control IgG (purified rabbit IgG, Innovative Research, Novi, MI) or 2 ng-10 ng/ml anti-S100A9 blocking antibody. Following virus adsorption, antibodies were added to the cells and the infection was carried out in the presence of the antibodies. In addition, in some experiments infection was done in the presence of purified S100A9 protein or HBSS buffer (vehicle control). Purified S100A9 protein (5 mg/ml) was added to S100A9 KO BMDMs following virus adsorption. Purified protein was present during infection.

siRNA. Control siRNA and mouse DDX21 siRNA were purchased from Santa Cruz Biotechnology. MH-S cells were transfected with 40 pmol of siRNAs using Lipofectamine 2000 (Invitrogen). At 48 h post-transfection, the cells were infected with IAV.

ELISA assay. Medium supernatant and mouse lung homogenate were analyzed for TNF and IL-6 levels by using a TNF and IL-6 specific ELISA kit (eBioscience, San Diego, CA). For S100A9 ELISA, Costar High-Binding 96-well plates (Corning, NY) were coated overnight at 4° C. with 800 ng/well of purified rabbit IgG against mouse S100A9 or 100 ng/well of goat polyclonal human S100A9 antibody (Abcam) diluted in 0.1 M carbonate buffer, pH 9.6. The wells were blocked with PBST+1% BSA for 1 h at room temperature. The samples were added and incubated overnight at 4° C. The plates were washed three times with PBST and incubated with either goat anti-mouse IgG (300 ng/well) (R&D) (for mouse S100A9) or mouse anti-human IgG (50 ng/well) (R&D) (for human S100A9) in PBST+0.1% BSA for 2 h at room temperature. The plates were then washed three times in PBST. To detect mouse S100A9, rabbit anti-goat HRP (Bio-Rad) was added to the plates. To detect human S100A9, goat anti-mouse HRP (Bio-Rad) was added. After 1 h incubation at room temperature, the plates were washed three times with PBST. TMB-S substrate (100 μl/well) (Sigma-Aldrich) was added to the plates according to the manufacturer's instructions. The ODs were detected at 450 nm, using a Modulas micro-plate reader.

To detect i.p.-injected S100A9 antibody in the lung homogenate, Costar High-Binding 96-well plates were coated overnight at 4° C. with mouse S100A9 protein diluted in 0.1 M carbonate buffer, pH 9.6. The wells were blocked with PBST+1% BSA for 1 h at room temperature. The lung homogenate was added and incubated overnight at 4° C. The plates were washed three times with PBST and goat anti-rabbit HRP (Bio-Rad) was added. After 1h of incubation at room temperature, the plates were washed three times with PBST. TMB-S substrate (100 μl/well) (Sigma-Aldrich) was added to the plates according to the manufacturer's instructions. ODs were detected at 450 nm by using a Modulas micro-plate reader.

IAV infection of mice. For survival experiments, 6-8-week old pathogen-free WT C57BL/6 mice (Jackson Laboratory) were injected i.p. with 2 mg/mouse of either control IgG or anti-S100A9 antibody. One day later, mice were anesthetized and inoculated via the intratracheal or I.T route with IAV ($1 \times 10^5$ pfu/mouse) in 100 μl of PBS (Invitrogen). Control mice were sham-inoculated with 100 μl of PBS. Survival was monitored until 8 days postinfection. For pathogenesis assay, mice were inoculated with IAV ($2 \times 10^4$ pfu/mouse via the I.T route) at 1 day after antibody treatment. At 3 days after infection, lungs and BALF were collected. Lung tissue sections were used for H&E analysis and in-situ TUNEL analysis. Lung homogenate was used for ELISA analysis (for TNF and IL-6). RT-PCR analysis for TNF and IL-6 expression was done with RNA isolated from mouse lungs. BALF was used for Western blotting with S100A9 antibody and S100A9 ELISA analysis.

In some experiments, purified mouse S100A9 protein (15 mg/mouse) diluted in PBS or HBSS buffer diluted in PBS (vehicle control) was administered to mice via the I.T route. At 8h post-treatment, TNF and IL-6 expression and production in the lung was monitored by RT-PCR and ELISA.

Immunohistochemistry. Lung sections from mock- or IAV-infected mice were stained with goat anti-mouse S100A9 antibody (1:100 dilution) (R&D) for 2 h at room temperature. After washing five times with PBS, lung sections were incubated with anti-goat Texas Red (1:50 dilution) (Vector Labs) for 1 h at room temperature. After washing three times with PBS, sections were mounted with DAPI containing mounting solution (Invitrogen). Sections were visualized by fluorescence microscopy.

In-situ TUNEL assay. To study apoptosis in the respiratory tract, TUNEL assays were done. Formalin-fixed lungs from IAV-infected mice were used. The TUNEL assay was done using an ApopTag Peroxidase In Situ Apoptosis Detection Kit (Milipore, MA). Digital images of TUNEL-stained lung sections were examined by light microscopy. Digital images were used to count the number of TUNEL-positive cells, using Image J software from NIH (available via the world wide web at rsbweb.nih.gov/ij/) as described previously (Mgbemena et al. (2012) J Immunol 189: 606-615). For each analysis, an area of $5.39 \times 10^2$ mm×$4.09 \times 10^2$ mm of TUNEL-stained lung section was scanned by Image J software. Gross apoptotic area was expressed as pixels per micron. This value was used to calculate the percentage of the apoptotic area in each analysis. Three IAV-infected mice treated with control IgG and three IAV-infected mice treated with S100A9 antibody were used. Data were collected from 9 areas per mouse from each experimental group. The values obtained from the 27 lung section areas of each experimental group were used for statistical analysis.

H&E staining. Hematoxylin and eosin (H&E) staining was performed on paraffin-embedded mouse lung sections. Briefly, slices of lung were sequentially rehydrated in 100% and 95% ethanol followed by xylene deparaffinization. After rinsing with distilled water, sections were stained with hematoxylin for 8 min and counterstained in eosin for 1 min followed by serial dehydration with 95% and 100% ethanol. Sections were then mounted on coverslips.

Apoptosis assay. Pathogen-associated molecular patterns (PAMPs) trigger host immune response by activating pattern recognition receptors like toll-like receptors (TLRs). However, the mechanism whereby several pathogens, including viruses, activate TLRs via a non-PAMP mechanism is unclear. Endogenous "inflammatory mediators" called damage-associated molecular patterns (DAMPs) have been implicated in regulating immune response and inflammation. However, the role of DAMPs in inflammation/immunity IAV-infected and S100A9 protein-treated cells were examined for apoptosis by annexin V labeling, using an annexin V/propidium iodide (PI) apoptosis detection kit (BioVision, CA) [75,78,79]. For TUNEL assay cells were grown in cover slips (12 mm diameter) (Ted-Pella, CA). TUNEL assay with macrophages was performed by using DeadEnd Colorimetric TUNEL System (Promega, WI). Digital images of TUNEL-stained macrophages were examined by light microscopy. Digital images were used to count the number of TUNEL-positive cells using Image J software (please see above). At least eight different fields were counted for each cover slip and two cover slips (duplicate) were examined for each experiment. Furthermore, each experiment was repeated independently three times.

Example 2

S100A9 blocking antibody reduces RSV viral titer following RSV infection. Mice were infected with respiratory syncytial virus (RSV) in the presence of either control antibody (IgG) or S100A9 blocking antibody (S100A9 Ab). At 3 days post-infection, the lungs of the mice were isolated and the RSV infectious virus titer was evaluated in the airways by performing plaque assay analysis with lung homogenate.

Figure 11:
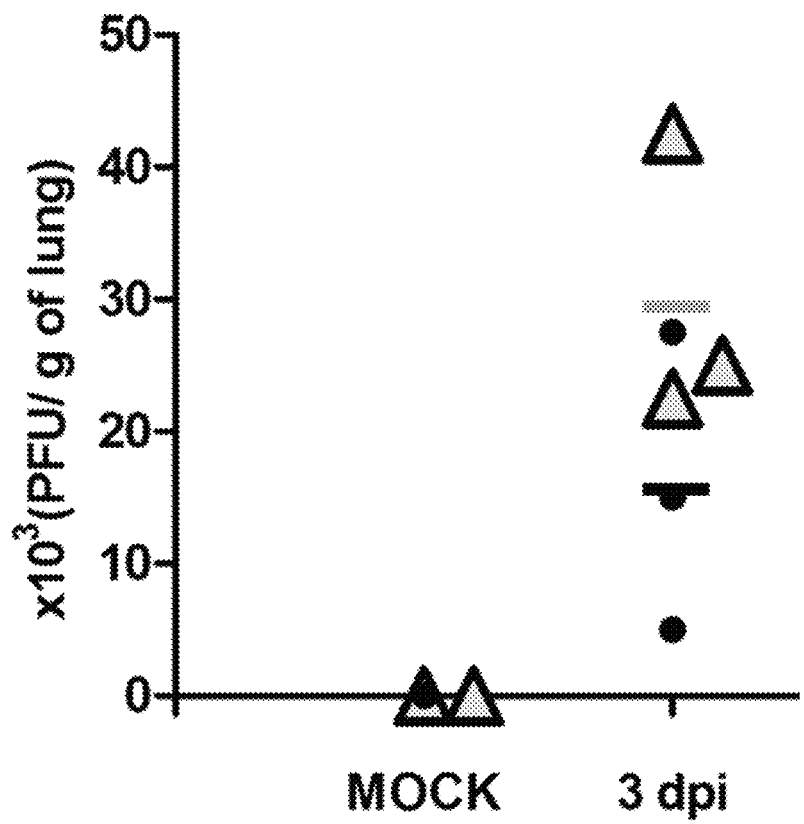
FIG. 11. RSV viral titer reduced in S100A9 Ab treated mice infected with RSV. Treatment with S100A9 blocking antibody (S100A9 Ab) demonstrated anti-viral properties to reduce RSV infection in the respiratory tract of mice compared to controls (treatment with IgG antibody).

As shown in FIG. 11, a reduced RSV viral titer was observed in S100A9 Ab treated mice. This result surprisingly indicated that S100A9 Ab may possess anti-viral properties that can reduce RSV infection in the respiratory tract of subjects. Accordingly, S100A9 Ab can be utilized as a therapeutic agent to combat RSV infection, since it may possess anti-viral activity and can reduce RSV burden in the airway of an infected subject.

Further experiments with macrophages will be conducted to elucidate the mechanism that may contribute to reduced RSV infection following blocking of extracellular S100A9 with S100A9 Ab, for example the examination of type I interferon (interferon-beta) response in macrophages and infected mice following S100A9 Ab administration given that interferon-beta is an essential anti-viral cytokine that restricts RSV infection.

Example 3

S100A9 blocking antibody reduces IL-6 production following RSV infection. A mouse alveolar macrophage cell line (MH-S) was infected with RSV in the presence of control IgG or S100A9 blocking antibody (S100A9 Ab). Thereafter, IL-6 production from the cells was assessed via ELISA.

Figure 12:
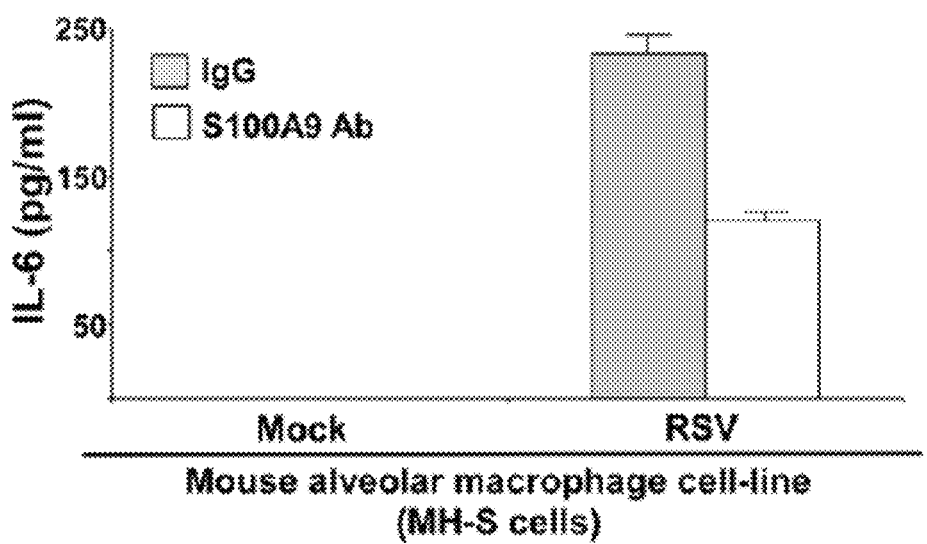
FIG. 12. IL-6 production reduced in S100A9 Ab treated MH-S cells infected with RSV. Treatment of MH-S cells with S100A9 blocking antibody (S100A9 Ab) resulted in reduced IL-6 production following RSV infection compared to controls (treatment with IgG antibody).

As shown in FIG. 12, treatment of MH-S cells with S100A9 Ab resulted in a reduction in IL-6 production following RSV infection. Pro-inflammatory cytokines such as IL-6 play a major role in exaggerating inflammation and pneumonia manifestation during RSV infection. This example demonstrates that blocking extracellular S100A9 protein with S100A9 Ab can diminish inflammation during RSV infection. Further studies with RSV infected mice will determine if treatment with S100A9 Ab can reduce RSV associated airway disease pathogenesis.

Example 4

Figure 13:
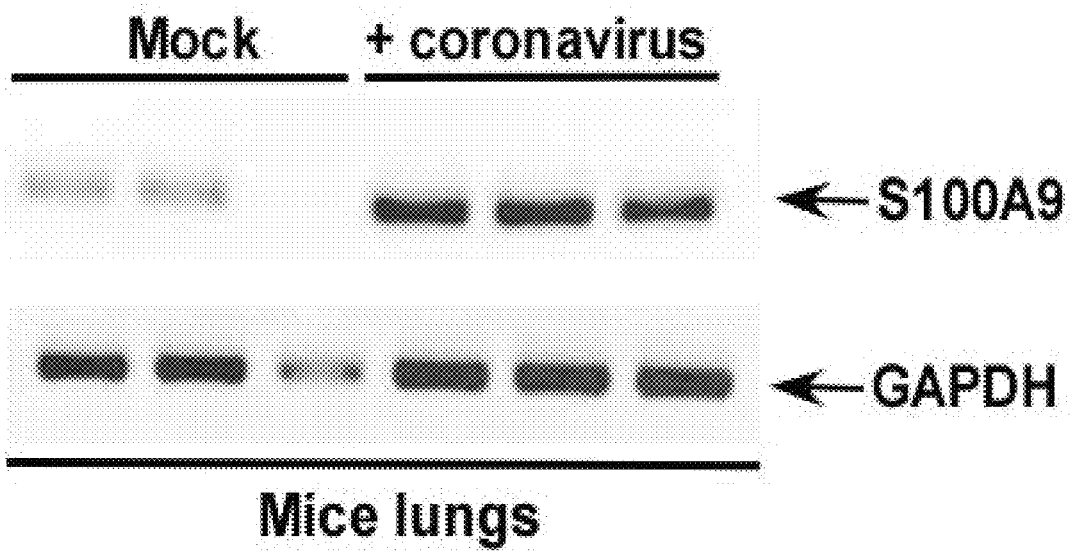
FIG. 13. A high expression of S100A9 is observed in the lungs of Coronavirus-infected mice. Mice were infected with mouse coronavirus (via intra-nasal route). Thereafter, the lungs were collected from mock infected and Coronavirus infected mice and analyzed for S100A9 expression by PCR.

S100A9 expression in lungs of coronavirus infected mouse. Mice were infected with mouse coronavirus (via intra-nasal route). Thereafter, the lungs collected from mock infected and coronavirus infected mice were analyzed for S100A9 expression by PCR. With reference to FIG. 13, the analysis confirmed the presence of S100A9 protein in the lungs of Coronavirus-infected mice.

As a treatment methodology, administration of an anti-S100A9 antibody to a particular subject could be utilized to mitigate the symptoms (e.g., inflammation) associated with a Coronavirus infection, such as, but not limited to, a COVID-19 infection. Moreover, administration of an anti-S100A9 antibody could be utilized as a prophylactic treatment for Coronavirus-induced lung inflammation.

Example 5

Humanized anti-S100A9 toxicology and use in human subjects. Administration of an anti-S100A9 antibody can be evaluated in a multi-step process. First, the anti-S100A9 antibody can undergo toxicology studies in accordance to good laboratory practices (GLP). For instance, toxicology studies of the anti-S100A9 antibody can be performed in primates (e.g., monkeys), as humanized anti-S100A9 binding is specific to humans and primates). Such studies can be performed for a sufficient time to establish appropriate toxicology parameters, for example 4-6 weeks in duration.

Second, a single ascending dose (SAD) study of the anti-S100A9 antibody can be performed in healthy human volunteers. Thereafter, a multiple ascending dose (MAD) study of the anti-S100A9 antibody can be performed in healthy human volunteers and/or in COVID-19 infected human patients.

Third, a Phase II/III study of the anti-S100A9 antibody can be performed in COVID-19 infected cells. For instance, the anti-inflammatory activity of humanized anti-S100A9 antibodies can be tested in human macrophages and lung epithelial cells that have been infected with COVID-19.

Figure 14:
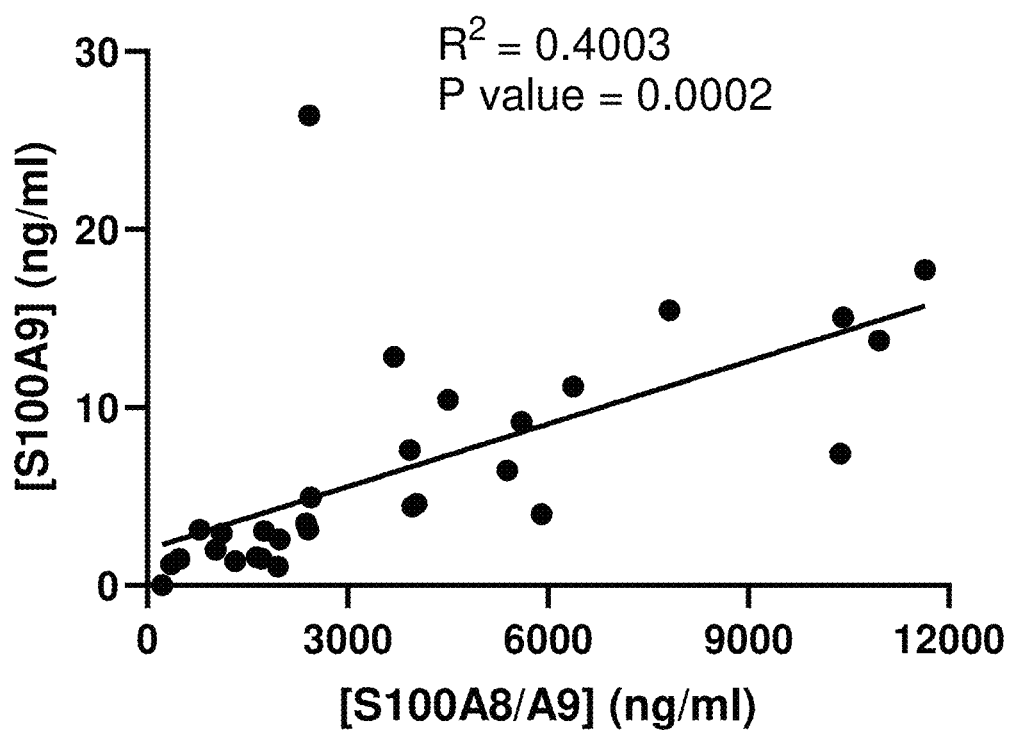
FIG. 14. Using ELISA, S100A9 and S100A8/A9 concentrations were measured in plasma of healthy patients and rheumatoid arthritis patients. S100A9 concentrations correlated with S100A8/A9 concentrations in the plasma.

Fourth, a Phase II/III study of the anti-S100A9 antibody can be performed in COVID-19 infected human patients and/or in at-risk human subjects. For instance, calprotectin can be utilized as a biomarker in human subjects, including for patient selection and/or for prediction of response. Moreover, pro-inflammatory cytokines (e.g., TNF, IL-6) concentrations in the patients can be measured as well as the concentrations of the pro-inflammatory cytokines with calprotectin levels in the patients. As shown in FIG. 14, S100A9 levels can be correlated with S100A8/A9 concentrations in plasma. Calprotectin can also be evaluated via commercial test that are available and known in the art.

Example 6

Human macrophages can be infected with coronavirus (e.g., SARS-CoV-2) in the absence of or in the presence of an anti-S100A9 antibody. Production of inflammatory cytokines (e.g. TNF, IL-6) by the infected macrophages can be measured by ELISA analysis.

Example 7

Mice expressing the human ACE2 receptor can be infected with coronavirus (e.g., SARS-CoV-2). These mice are known to develop severe pneumonia due to exaggerated airway inflammation. In addition, these mice are susceptible to SARS-COV-2 infection since after 6 days post-infection, the survival rate of the infected mice is approximately 50%.

In prophylactic studies, mice can be administered an anti-S100A9 antibody (e.g., via an intra-peritoneal or via intra-tracheal routes of administration) at 1 day or at 2 days prior to infection, followed by infection (via i.t. route) of the mice with SARS-CoV-2 in the presence of anti-S100A9 antibody (via i.p. or i.t. route). Mice survival studies can be conducted and airway inflammatory and disease status can be monitored using various methods, including ELISA analysis of lung inflammatory cytokines and histopathological analysis of H&E stained lungs to deduce pneumonia/inflammation score.

In therapeutic studies, an anti-S100A9 antibody can be administered (via i.p. or i.t. routes) at time periods of 12 hours, 1 day, and 2 days post-infection. The studies can be conducted in a similar manner as described above.

Further, anti-S100A9 antibody can be administered to high-risk individuals as an aerosol spray. For instance, anti-S100A9 antibody can be administered to patients infected with coronavirus (e.g., SARS-CoV-2) via Pulmonary Drug Delivery (PDD) system or via an intravenous route.

The invention claimed is:

1. A method of treating a Coronavirus-induced lung infection by reducing lung inflammation without substantially affecting Coronavirus viral burden in a subject, said method comprising the step of administering a composition comprising an anti-S100A9 antibody to the subject in need thereof, wherein the composition reduces lung inflammation in the subject, and wherein the composition does not substantially affect Coronavirus viral burden in the subject.

2. The method of claim 1, wherein the composition is administered to the subject via a route selected the group consisting of inhalation to the respiratory system, instillation in the respiratory system, intraperitoneal injection, and intravenous injection.

3. The method of claim 1, wherein the anti-S100A9 antibody is a humanized anti-S100A9 antibody.

4. The method of claim 1, wherein the anti-S100A9 antibody reduces apoptosis in one or more lungs of the subject.

5. The method of claim 1, wherein the administration of the composition reduces activation of the TLR4-MyD88 pathway in the subject.

6. The method of claim 1, wherein the administration of the composition reduces TNF-α in a lung of the subject.

7. The method of claim 1, wherein the administration of the composition reduces IL-6 in the subject.

8. The method of claim 1, wherein the composition consists essentially of the anti-S100A9 antibody.

9. The method of claim 1, wherein the composition consists of the anti-S100A9 antibody.

10. The method of claim 1, wherein the method further comprises administering a second therapeutic agent in conjunction with the anti-S100A9 antibody, wherein the second therapeutic agent is an antiviral drug.

11. The method of claim 10, wherein the second therapeutic agent is selected from the group consisting of amantadine, oseltamivir, zanamivir, ribavirin, and palivizumab.

12. A method of prophylactically treating a Coronavirus-induced lung inflammation by reducing lung inflammation without substantially affecting Coronavirus viral burden in a subject, said method comprising the step of administering a composition comprising an anti-S100A9 antibody to the subject wherein the composition is effective to reduce Coronavirus-induced lung inflammation in the subject, and wherein the composition does not substantially affect Coronavirus viral burden in the subject.

13. The method of claim 12, wherein the composition is administered to the subject via a route selected the group consisting of inhalation to the respiratory system, instillation in the respiratory system, intraperitoneal injection, and intravenous injection.

14. The method of claim 12, wherein the anti-S100A9 antibody is a humanized anti-S100A9 antibody.

15. The method of claim 12, wherein the administration of the composition reduces activation of the TLR4-MyD88 pathway in the subject.

16. The method of claim 12, wherein the composition consists essentially of the anti-S100A9 antibody.

17. The method of claim 12, wherein the composition consists of the anti-S100A9 antibody.

18. The method of claim 1, wherein the method wherein the administration of the composition reduces activation of the TLR4-MyD88 pathway in the subject in the absence of S100A8.

19. The method of claim 12, wherein the method wherein the administration of the composition reduces activation of the TLR4-MyD88 pathway in the subject in the absence of S100A8.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: GAPDH forward primer sequence

<400> SEQUENCE: 1
gtcagtggtg gacctgacct                                              20

<210> SEQ ID NO 2
<211> LENGTH: 20
<212> TYPE: DNA
<213> ORGANISM: Artificial Sequence
<220> FEATURE:
<223> OTHER INFORMATION: GAPDH reverse  primer sequence

<400> SEQUENCE: 2
aggggtctac atggcaactg                                              20

<210> SEQ ID NO 3
<211> LENGTH: 26
<212> TYPE: DNA
<213> ORGANISM: Artificial Sequence
<220> FEATURE:
<223> OTHER INFORMATION: Mouse GAPDH forward primer sequence

<400> SEQUENCE: 3
```

```
gccaaggtca tccatgacaa ctttgg                                          26

<210> SEQ ID NO 4
<211> LENGTH: 26
<212> TYPE: DNA
<213> ORGANISM: Artificial Sequence
<220> FEATURE:
<223> OTHER INFORMATION: comment Mouse GAPDH reverse primer sequence

<400> SEQUENCE: 4
gcctgcttca ccaccttctt gatgtc                                          26

<210> SEQ ID NO 5
<211> LENGTH: 20
<212> TYPE: DNA
<213> ORGANISM: Artificial Sequence
<220> FEATURE:
<223> OTHER INFORMATION: Mouse S100A9 forward primer sequence

<400> SEQUENCE: 5
gtcctggttt gtgtccaggt                                                 20

<210> SEQ ID NO 6
<211> LENGTH: 20
<212> TYPE: DNA
<213> ORGANISM: Artificial Sequence
<220> FEATURE:
<223> OTHER INFORMATION: Mouse S100A9 reverse primer sequence

<400> SEQUENCE: 6
tcatcgacac cttccatcaa                                                 20

<210> SEQ ID NO 7
<211> LENGTH: 20
<212> TYPE: DNA
<213> ORGANISM: Artificial Sequence
<220> FEATURE:
<223> OTHER INFORMATION: Mouse DDX21 forward primer sequence

<400> SEQUENCE: 7 gatccccta aatccaggaa                                                  20

<210> SEQ ID NO 8
<211> LENGTH: 20
<212> TYPE: DNA
<213> ORGANISM: Artificial Sequence
<220> FEATURE:
<223> OTHER INFORMATION: Mouse DDX21 reverse primer sequence

<400> SEQUENCE: 8
ttcggaaggc tcctctgtta                                                 20

<210> SEQ ID NO 9
<211> LENGTH: 20
<212> TYPE: DNA
<213> ORGANISM: Artificial Sequence
<220> FEATURE:
<223> OTHER INFORMATION: Mouse TNF- forward primer sequence

<400> SEQUENCE: 9
cctgtagccc acgtcgtagc                                                 20

<210> SEQ ID NO 10
<211> LENGTH: 20
<212> TYPE: DNA
<213> ORGANISM: Artificial Sequence
```

```
<220> FEATURE:
<223> OTHER INFORMATION: Mouse TNF- reverse primer sequence

<400> SEQUENCE: 10
ttgacctcag cgctgagttg                                              20

<210> SEQ ID NO 11
<211> LENGTH: 22
<212> TYPE: DNA
<213> ORGANISM: Artificial Sequence
<220> FEATURE:
<223> OTHER INFORMATION: Mouse IL-6 forward primer sequence

<400> SEQUENCE: 11
ttgccttctt gggactgatg ct                                           22

<210> SEQ ID NO 12
<211> LENGTH: 22
<212> TYPE: DNA
<213> ORGANISM: Artificial Sequence
<220> FEATURE:
<223> OTHER INFORMATION: Mouse IL-6 reverse primer sequence

<400> SEQUENCE: 12
gtatctctct gaaggactct gg                                           22

<210> SEQ ID NO 13
<211> LENGTH: 18
<212> TYPE: DNA
<213> ORGANISM: Artificial Sequence
<220> FEATURE:
<223> OTHER INFORMATION: IAV HA forward primer sequence

<400> SEQUENCE: 13
cccaaggaaa gttcatgg                                                18

<210> SEQ ID NO 14
<211> LENGTH: 20
<212> TYPE: DNA
<213> ORGANISM: Artificial Sequence
<220> FEATURE:
<223> OTHER INFORMATION: IAV HA reverse primer sequence

<400> SEQUENCE: 14
gaacacccca tagtacaagg                                              20

<210> SEQ ID NO 15
<211> LENGTH: 114
<212> TYPE: PRT
<213> ORGANISM: Homo sapiens

<400> SEQUENCE: 15

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
```

-continued

```
                85                  90                  95
Gly Asp Glu Gly Pro Gly His His His Lys Pro Gly Leu Gly Glu Gly
            100                 105                 110
Thr Pro
```